United States Patent [19]

Asmus

[11] Patent Number: 5,369,155
[45] Date of Patent: Nov. 29, 1994

[54] COMPOSITE OF A DISPERSED GEL IN AN ADHESIVE MATRIX AND METHOD FOR PREPARING SAME

[75] Inventor: Robert A. Asmus, Hudson Township, St. Croix County, Wis.

[73] Assignee: Minnesota Mining and Manufacturing Company, St. Paul, Minn.

[21] Appl. No.: 86,324

[22] Filed: Jul. 1, 1993

Related U.S. Application Data

[60] Division of Ser. No. 905,490, Jun. 25, 1992, Pat. No. 5,270,358, which is a continuation of Ser. No. 827,500, Jan. 24, 1992, abandoned, which is a continuation of Ser. No. 458,246, Dec. 28, 1989, abandoned.

[51] Int. Cl.$^5$ .............. C08J 3/20; C08K 5/05; C08L 89/00
[52] U.S. Cl. .................. 524/55; 523/111; 524/22; 524/27; 524/388
[58] Field of Search .............. 524/22, 27, 55, 388; 523/111

[56] References Cited

U.S. PATENT DOCUMENTS

| | | | |
|---|---|---|---|
| 3,612,053 | 10/1971 | Pratt | 128/283 |
| 3,928,262 | 12/1975 | Ono et al. | 260/17 R |
| 4,166,051 | 8/1979 | Cilento et al. | 260/17.4 CL |
| 4,253,460 | 3/1981 | Chen et al. | 128/283 |
| 4,300,820 | 11/1981 | Shah | 351/160 H |
| 4,306,551 | 12/1981 | Nymes et al. | 128/156 |
| 4,307,717 | 12/1981 | Nymes et al. | 128/156 |
| 4,310,509 | 1/1982 | Berglund et al. | 424/28 |
| 4,323,527 | 4/1982 | Rosso et al. | 424/28 |
| 4,337,325 | 6/1982 | Shah | 525/205 |
| 4,356,819 | 11/1982 | Potaczek | 128/156 |
| 4,369,229 | 1/1983 | Shah | 428/421 |
| 4,438,258 | 3/1984 | Graham | 528/361 |
| 4,496,357 | 1/1985 | Osburn | 604/336 |
| 4,505,976 | 3/1985 | Doehnert et al. | 428/355 |
| 4,552,138 | 11/1985 | Hofeditz et al. | 128/156 |
| 4,554,924 | 11/1985 | Engel | 128/640 |
| 4,588,762 | 5/1986 | Mruk et al. | 524/45 |
| 4,593,053 | 6/1986 | Jeune et al. | 523/111 |
| 4,650,817 | 3/1987 | Allen, Jr. et al. | 523/105 |
| 4,693,887 | 9/1987 | Shah | 424/19 |
| 4,701,509 | 10/1987 | Sun et al. | 526/264 |
| 4,830,776 | 5/1989 | Thompson | 252/500 |
| 4,846,185 | 7/1989 | Carim | 128/641 |
| 4,848,353 | 7/1989 | Engel | 128/640 |
| 4,904,247 | 2/1990 | Therriault et al. | 604/304 |
| 4,908,403 | 3/1990 | Spada et al. | 524/239 |
| 4,943,461 | 7/1990 | Karim | 428/40 |
| 5,024,227 | 6/1991 | Schmid | 128/640 |

FOREIGN PATENT DOCUMENTS

| | | | |
|---|---|---|---|
| 0072607 | 4/1982 | European Pat. Off. | A61F 5/44 |
| 0066887 | 6/1982 | European Pat. Off. | A61F 5/44 |
| 0072251 | 8/1982 | European Pat. Off. | A61L 15/06 |
| 0085327 | 1/1983 | European Pat. Off. | A61B 5/04 |
| 0297769 | 6/1988 | European Pat. Off. | A61L 15/06 |
| 0307187 | 8/1988 | European Pat. Off. | A61L 15/03 |
| 0318183 | 11/1988 | European Pat. Off. | A61L 25/00 |
| 0322098 | 11/1988 | European Pat. Off. | C08F 226/06 |
| 2008000 | 11/1978 | United Kingdom | A61L 15/06 |
| 2046774 | 3/1980 | United Kingdom | C08B 37/00 |
| 2061732 | 9/1980 | United Kingdom | A61F 13/00 |
| 86/05083 | 12/1986 | WIPO | A61B 5/04 |
| 88/01877 | 3/1988 | WIPO | A61L 15/06 |

OTHER PUBLICATIONS

Stucker et al., "Butyl Rubber and Polyisobutylene" in *Butyl Rubber & Polyisobutylene in Adhesives & Sealants*, pp. 225-269 (1977).

Primary Examiner—Paul R. Michl
Assistant Examiner—P. Niland
Attorney, Agent, or Firm—Gary L. Griswold; Walter N. Kirn; John H. Hornickel

[57] ABSTRACT

A composite of a gel of swollen hydrocolloid dispersed in a pressure sensitive adhesive matrix is provided. The gel has a natural or synthetically derived hydrocolloid swollen with a non-volatile swelling agent, such that the gel may have a shear modulus of less than $6.2 \times 10_6$ dynes/cm$^2$ The gel-adhesive composite has continued skin adhesion whether applied to or existing in dry or moist skin conditions. The gel contributes a high moisture vapor transmission rate to attempt to maintain dry skin conditions while the adhesive maintains skin adhesion. The gel-adhesive composite may be used in a variety of tape, dressing, bandage, drape, or other skin contacting usage and may optionally include antimicrobial agents to treat the skin while adhesion continues.

8 Claims, 1 Drawing Sheet

COMPOSITE OF A DISPERSED GEL IN AN ADHESIVE MATRIX AND METHOD FOR PREPARING SAME

This is a division of application Ser. No. 07/905,490 filed Jun. 25, 1992, now U.S. Pat. No. 5,270,358 which is a file wrapper continuation of application Ser. No. 07/827,500 filed Jan. 24, 1992, now abandoned, which is a file wrapper continuation of application Ser. No. 07/458,246 filed Dec. 28, 1989, now abandoned.

FIELD OF THE INVENTION

The present invention relates to novel composites of gels of swollen hydrocolloids dispersed in a pressure sensitive adhesive matrix. The present invention also relates to the preparation of such composites, which are useful in medical applications, such as tapes, dressings, drapes, and antimicrobial devices.

BACKGROUND OF THE INVENTION

A hydrocolloid is a synthetically prepared or naturally occurring polymer capable of forming a thickened gel in the presence of water and polyols.

Hydrogels, hydrocolloids swollen with water or another hydrophilic liquid have been known for the purpose of absorbing or retaining moisture or water. U.S. Pat. Nos. 4,438,258 and 4,552,138 describe typical hydrogels.

In medical applications, hydrogels swollen with water or other liquids generally have good moisture vapor transmission rates. Hydrogels are quite useful for the absorbing or removal of body fluids, such as perspiration, from the pores of the continuous skin of the patient or from a wound, incision or other opening in the skin of the patient.

While certain hydrogels can have some pressure sensitive adhesive properties, the adhesive strength of hydrogels is marginal for general utility skin adhesives. Hydrogels alone are generally not used as medical tapes, dressings, drapes and the like because of lack of good adhesive strength in either dry skin environments ("dry stick adhesion") or in moist skin environments ("wet stick adhesion"). Both of these environments require continuous strong adhesion of a tape, dressing, bandage or the like for proper patient care.

On the other hand, conventional pressure sensitive adhesives have strong dry stick adhesion, but often lack high moisture vapor transmission properties. For this reason, the adhesion may fail in moist environments occurring beneath medical tapes, dressings, drapes and the like.

Also, if antimicrobial agents, such as chlorhexidine, are desired to be administered topically to the skin of the patient, these pressure sensitive adhesives alone are poor candidates to provide rapid delivery of the antimicrobial agent to the skin.

Conventional pressure sensitive adhesives have been mixed with unswollen hydrocolloidal filler material for the purpose of providing wet stick adhesion where initial moist skin environments are common. For example, U.S. Pat. Nos. 4,166,051 and 4,505,976 describe adhesives with hydrocolloids mixed therein. These mixtures are used as sealants about a skin opening of a patient, such as a stoma, following surgery.

A stoma sealant requires wet stick adhesion to absorb or wick away moisture or other body fluids from about the skin opening. However, the use of unswollen hydrocolloidal fillers or reinforcers initially make the adhesive much stiffer and less pliable, reducing the dry stick adhesion of the adhesive against the flexible contours of the movable and stretchable skin.

Furthermore, following the continued absorbance of moisture and other body fluids, inevitably, wet stick adhesion is also reduced. Also such stoma-type adhesives are typically opaque, which, while not important for their usefulness about stomas, limit their usefulness where transparent or nearly transparent adhesives are desired in medical applications such as for incise drapes.

Thus, the use of hydrocolloids in the medical applications has progressed in diverging directions. In one direction, swollen hydrocolloids. Hydrogels provide high moisture vapor transmission rates but without significant dry or wet stick adhesive strength. In the other direction, unswollen hydrocolloids mixed into conventional pressure sensitive adhesives to become opaque stoma-type sealants provide wet stick adhesion at the expense of dry stick adhesion.

What is needed in the art is a composite which has the good dry stick adhesion of a strong pressure sensitive adhesive and the high moisture vapor transmission rate of a swollen hydrocolloid. It is desirable to have a composite which has the capability of avoiding loss of adhesion against the skin or skin opening upon continued exposure to moist conditions. It is also desirable to have an adhesive which has translucency approaching transparency and has the ability to release antimicrobial agents in efficacious amounts when placed in contact with the skin.

SUMMARY OF THE INVENTION

The present invention provides a composite of a gel dispersed in an adhesive matrix which continuously transmits moisture vapor while continuously adhered to the skin of a patient. The gel-adhesive composite of the present invention is at least nearly transparent, has a high moisture vapor transmission rate, and has a high peel strength.

The composite is a two phase system of gel and adhesive, where the dispersed phase of the system is a two component gel.

The gel-adhesive composite requires at least three components: (1) a pressure sensitive adhesive as the continuous matrix; and in the dispersed gel, (2) a hydrocolloid and (3) a swelling agent for the hydrocolloid.

The gel-adhesive composite comprises from about 5 weight percent to about 99 weight percent of a pressure sensitive adhesive composition and from about 1 weight percent to about 95 weight percent of a gel dispersed in the pressure sensitive adhesive composition, the gel comprising a hydrocolloid and a non-volatile hydrocolloid swelling agent having a ratio of weight fractions of hydrocolloid to swelling agent of from about 3:1 to about 1:99.

The pressure sensitive adhesive may be a conventional pressure sensitive adhesive, which is defined by the Pressure Sensitive Tape Council (*Glossary of Terms Used in Pressure Sensitive Tape Industry*, PSTC, Glenview, Ill. 1959) to be adhesives "which in dry form are aggressively and permanently tacky at room temperature and firmly adhere to a variety of dissimilar surfaces upon mere contact without the need of more than finger or hand pressure." These adhesives "have a sufficiently cohesive holding and elastic nature so that, despite their aggressive tackiness, they can be handled with the fingers and removed from smooth surfaces without leaving a residue." Because pressure sensitive adhesives vary in their strength of adhesiveness, their selection for use in the composite will depend on the final application desired.

The pressure sensitive adhesive is preferably hydrophobic, i.e., tending neither to combine with nor be soluble in water. The natural lack of affinity for water possessed by a hydrophobic pressure sensitive adhesive causes it to separate from and remain immiscible with water or other hydrophilic liquids.

The swelling agent is a hydrophilic liquid, i.e., tending to combine with and be soluble in water. The natural affinity for water of the swelling agent allows the swelling agent to swell the hydrocolloid, defined above, keeping the swollen hydrocolloid, the gel, separated from and dispersed in the pressure sensitive adhesive.

The difference in hydrophilicity of the swelling agent to the pressure sensitive adhesive sufficient to generate a two phase system, i.e., their incompatibility, is required to maintain sufficient amounts of swelling agent in the hydrocolloidal gel particles dispersed in the pressure sensitive adhesive matrix and to minimize plasticization of the pressure sensitive adhesive, which would cause loss of skin adhesion and increase adhesive residue. Optimally, no amount of swelling agent should migrate into the pressure sensitive adhesive. Preferably, less than 0.5 weight percent of the pressure sensitive adhesive matrix should comprise migrated swelling agent. In no event should more than 5 weight percent of the pressure sensitive matrix comprise migrated swelling agent. In no event should the amount of swelling agent migrated into the pressure adhesive matrix cause the gel to have a ratio of weight fractions of hydrocolloid to swelling agent exceeding about 3:1.

The swelling agent must also be non-volatile, i.e., essentially non-evaporative either at ambient temperatures and pressures or at elevated temperatures used in processing to prepare the gel-adhesive composite. Non-volatile swelling agents allow the gel to remain a gel after processing and during use, preserving the swollen condition of the hydrocolloid for its high moisture vapor transmission properties.

Thus, gel-adhesive composite of the present invention retains the high peel adhesion and high shear adhesion properties of the pressure sensitive adhesive in the presence of moisture vapor and other fluids because the high moisture vapor transmission rate property provided by the gel facilitates removal of the moisture or other fluid from the area where the composite is adhered.

The gel-adhesive composite requires at least the pressure sensitive adhesive and the gel of hydrocolloid and swelling agent. Without the pressure sensitive adhesive, the gel may not be strong enough as an adhesive to provide continued adhesion in dry or moist skin conditions. Without the hydrocolloid, no gel can form, and the hydrophilic swelling agent would "bloom" to the surface of the adhesive, thus severely degrading adhesion. Without the swelling agent, the unswollen hydrocolloid in the adhesive may greatly reduce continued dry stick adhesion capability.

The gel-adhesive composite may also include a broad spectrum antimicrobial agent therein to provide medicinal treatment while the composite is adhered to the skin of the patient.

The composite may be coated on a backing material or web also preferably having a high moisture vapor transmission rate to provide strength to the composite and protection from exposure of the skin of the patient to the surrounding environment. The composite resists the loss of adhesion to skin when exposed to moisture, water, exudate, or other fluid present in or about the skin or the skin opening.

The composite of the present invention is prepared by dispersing a gel of hydrocolloids swollen with a swelling agent into a strong pressure sensitive adhesive. Alternatively, the gel and the adhesive may be mixed in a latex solution. Either way, the other solvents used in preparing the gel and/or the pressure sensitive adhesive are removed, principally by evaporation, to yield the gel-adhesive composite.

The gel-adhesive composites of the present invention are achievements of the balancing of two important properties for medical adhesives involving the adhering of a material to the skin or skin opening: (1) significant adhesive strength in dry or moist conditions continuously for an extended period which does not exhaust itself upon initial swelling of hydrocolloidal material, and (2) a high moisture vapor transmission rate. The composites of the present invention bridge the gap between high moisture vapor transmission rates provided by hydrogels and significant adhesive strength provided by conventional pressure sensitive adhesives.

Consequently, balancing these properties permits the composites of the present invention to provide utility for a wide variety of skin adhesive applications. Nearly transparent composites have great utility as incise drapes, dressings, bandages, tapes of all varieties for use on skin, and other skin contacting uses.

EMBODIMENTS OF THE INVENTION

THE GEL-ADHESIVE COMPOSITE

Figure 2:
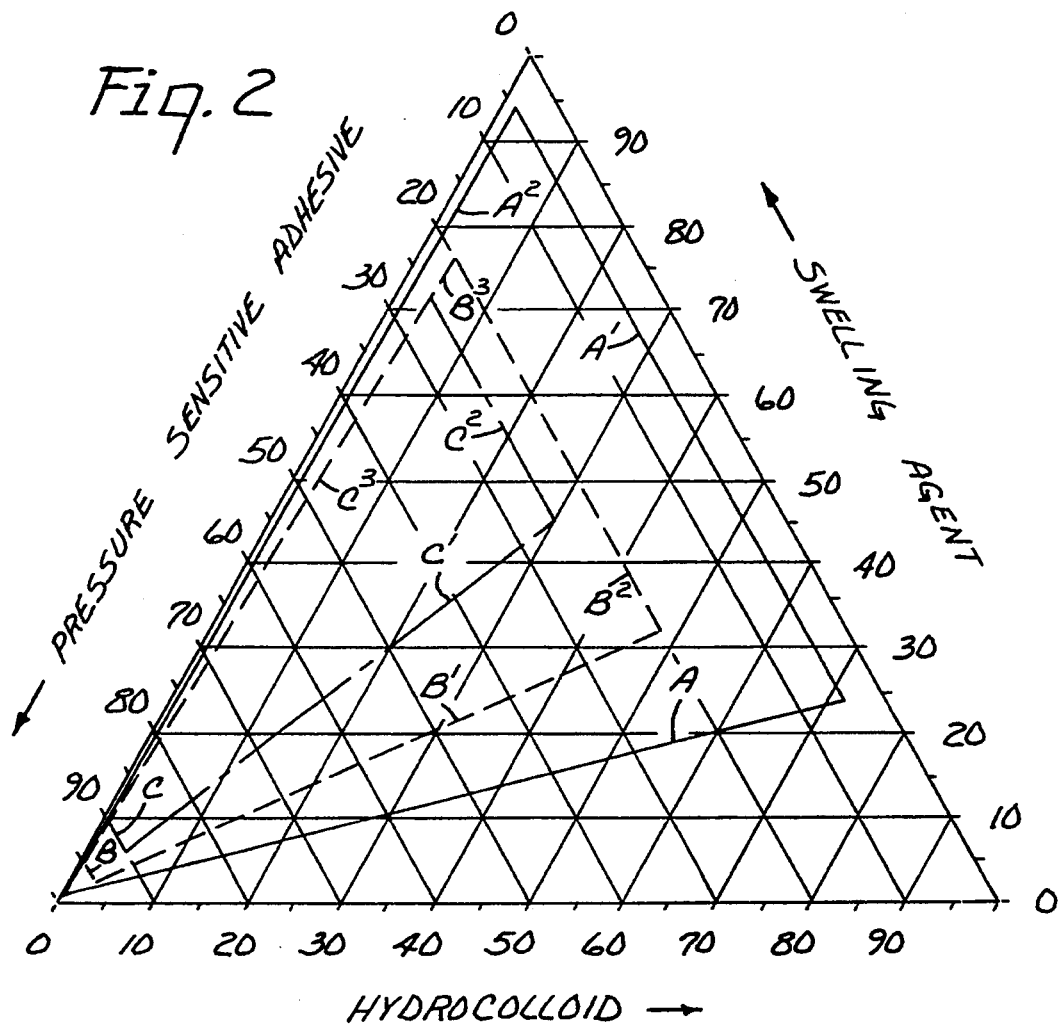
FIG. 2 is a tri-coordinate graph depicting various ranges of weight fractions of pressure sensitive adhesive, hydrocolloid, and swelling agent used to prepare a gel-adhesive composite within the scope of the present invention.

The gel-adhesive composite of the present invention comprises a two phase system. When used in medical applications, the composite adheres to the surface of the skin of the patient and maintains that surface in as dry an environment as can occur where the skin or skin opening exudes perspiration, or other body fluids.

THE PRESSURE SENSITIVE ADHESIVE

In medical application, the pressure sensitive adhesive must be tacky at room temperature as well as at skin temperature of patients. Also, the adhesive must be dermatogically acceptable, i.e., after continuous contact with skin, there is little adhesive residue upon removal and there is no significant reaction with skin during adhesion.

The strength of the pressure sensitive adhesive phase of the composite depends on the type of pressure sensitive adhesive chosen. The adhesives must provide sufficient adhesive strength to adhere the gel-adhesive composite to the skin of the patient.

The pressure sensitive adhesives may be polymeric adhesive compositions prepared from a combination of monomers, homopolymers, copolymers and tackifiers, or blends thereof to produce polymeric adhesive compositions containing polyacrylates, polyolefins, silicone adhesives, natural or synthetically derived rubber base adhesives, or polyvinyl ethers.

Preferably, the pressure sensitive adhesives useful in the composite are hydrophobic allowing the adhesives of the pressure sensitive adhesive to resist absorbing either hydrophilic swelling agent from the dispersed gel or moisture or other body exudate gathering at the skin or skin opening during use. The composite retains its strong adhesiveness even in the presence of water and swelling agents since the pressure sensitive adhesive is unaffected and not plasticized by these agents. Excess moisture is taken away from the skin surface by the gel having a high moisture vapor transmission rate. This prohibits adhesion loss due to pooling of moisture under the adhesive against the skin.

The pressure sensitive adhesive optimally should not absorb any swelling agent and preferably less than 0.5 weight percent of its weight. It has been found that the pressure sensitive adhesive may absorb swelling agent in amounts up to 5 weight percent of its weight in certain circumstances without overly plasticizing the pressure sensitive adhesive.

Preferred adhesives are acrylic pressure-sensitive adhesive copolymers comprising "A" and "B" monomers as follows: Monomer A is a hydrophobic monomeric acrylic or methacrylic acid ester of alkyl alcohol, the alkyl alcohol containing 4 to 10 carbon atoms, preferably 6 to 10 carbon atoms, more preferably 6 to 8 carbon atoms, and most preferably 8 carbon atoms. Examples of suitable A monomers are n-butyl, n-pentyl, n-hexyl, isoheptyl, n-nonyl, n-decyl, isohexyl, 2-ethyloctyl, isooctyl and 2-ethylhexyl acrylates. The most preferred monomer is isooctyl acrylate.

Monomer B is a reinforcing monomer comprising acrylic acid; methacrylic acid; alkyl acrylates and methacrylates containing 1 to 3 carbon atoms in the alkyl group; acrylamide; methacrylamide; lower alkyl-substituted acrylamides (i.e., the alkyl group containing 1 to 4 carbon atoms) such as tertiary-butyl acrylamide; diacetone acrylamide; N-vinyl-2-pyrrolidone; vinyl ethers such as vinyl tertiary-butyl ether; substituted ethylenes such as derivatives of maleic anhydride, dimethyl itaconate and monoethylformate; or vinyl perfluoro-n-butyrate. The preferred B monomers are acrylic acid, acrylamide and N-vinyl-2-pyrrolidone. The most preferred B monomer is N-vinyl-2-pyrrolidone.

The A monomer in such copolymer is present in the pressure sensitive adhesive copolymer in an amount by weight of about 85 to 98 percent by weight, and preferably about 90 to 98 percent by weight of the weight of all monomers in the copolymer.

The B monomer in such a copolymer is present in the pressure sensitive adhesive copolymer in an amount by weight of about 2 to about 15 percent by weight, and preferably about 2 to 10 percent by weight of the weight of all monomers in the copolymer.

Most preferably, the pressure sensitive adhesive of the present invention is an isooctyl acrylate/N-vinyl pyrrolidone copolymer in a weight fraction ratio of 91:9.

The adhesive copolymers of the above type are known and their method of preparation is well known to those skilled in the art, having been described for example, in U.S. Pat. No. Re: 24,906 of Ulrich, incorporated herein by reference. Since the pressure sensitive adhesives described above are inherently rubbery and tacky and are suitably heat and light stable, there is no need to add tackifiers, crosslinkers, or stabilizers. However, such may be added if desired.

The availability and preparation of other pressure sensitive adhesives useful in the present invention are described in the literature. In the *Handbook of Pressure Sensitive Adhesive Technology* 2nd Ed., Satas, Editor, (Von Nostrand Reinhold, New York 1989), a number of types of useful pressure sensitive adhesives are discussed: natural rubber adhesives; A-B-A block copolymers, (such as polystyrene-polybutadiene-polystyrene (S-B-S), polystyrene-polyisoprene-polystyrene (S-I-S), polystyrene-poly(ethylene/butylene)-polystyrene (S-EB-S), and polystyrene-poly(ethylene/propylene)-polystyrene (S-EP-S) polymers); butyl rubbers and polyisobutylene; vinyl ether polymers; silicones; polyisoprene; butadiene acrylonitrile rubber; polychloroprene; atactic polypropylene; and additional descriptions of acrylic adhesives and acrylic dispersions. Any of these pressure sensitive adhesives may form the polymeric matrix into which the gel may be dispersed.

Desirably among these available pressure sensitive adhesives, silicone pressure sensitive adhesives (such as those disclosed in U.S. Pat. No. 4,039,707 incorporated by reference) and polystyrene-polyisoprene-polystyrene A-B-A block copolymers (such as those disclosed in U.S. Pat. No. 3,935,338 incorporated by reference) are useful.

THE GEL OF HYDROCOLLOID AND SWELLING AGENT

The gel of the gel-adhesive composite is hydrophilic to the extent necessary to maintain a dispersion of gel particles in the pressure sensitive adhesive matrix. At the surface of and throughout the composite, the gel particles provide the mechanism to remove the moisture or other body exudate from the skin or skin opening. While the gel may have its own pressure sensitive adhesive properties, it is not necessary. The adhesive matrix provides the necessary adhesiveness which is maintained by the gel's moisture vapor transmission properties.

The gel in the gel-adhesive composite comprises the hydrocolloid solid and the swelling agent liquid. The ratio of these two constituents of the gel is important to the functioning of the composite. The ratio of the swelling agent to the hydrocolloid and the ratio of the gel to the adhesive provide the basis for balancing the adhesive and moisture vapor transmitting properties of the composite.

THE HYDROCOLLOID

The hydrocolloid used in the present invention may be any synthetically prepared or naturally occurring polymer capable of forming a thickened gel in the presence of the swelling agent. Varieties of hydrocolloids within the scope of the present invention include synthetic polymers prepared from single or multiple monomers, naturally occurring hydrophilic polymers or chemically modified naturally occurring hydrophilic polymers.

Non-limiting examples of such hydrocolloids include polyhydroxyalkyl acrylates and methacrylates, polyvinyl lactams, polyvinyl alcohols, polyoxyalkylenes, polyacrylamides, polyacrylic acid, polystyrene sulfonates, natural or synthetically modified polysaccarides, alginates, xanthan gums, guar gums, and cellulosics.

When used in medical applications, the hydrocolloid must also be dermatologically acceptable and non-reactive with the skin of the patient or other components of the gel-adhesive composite including any antimicrobial agents which may be present in the composite.

Desirably, the hydrocolloid is a synthetic polymer which may be either linear or crosslinked. Non-limiting examples of synthetic hydrocolloids include polymers prepared from N-vinyl lactams, e.g. N-vinyl-2-pyrrolidone, 5-methyl-N-vinyl-2-pyrrolidone, 5-ethyl-N-vinyl-2-pyrrolidone, 3,3-dimethyl-N-vinyl-2- pyrrolidone, 3-methyl-N-vinyl-2-pyrrolidone, 3-ethyl-N-vinyl-2-pyrrolidone, 4-methyl-N-vinyl-2-pyrrolidone, 4-ethyl-N-vinyl-2-pyrrolidone, N-vinyl-2-valerolactam, and N-vinyl-2-caprolactam.

Other monomers useful to prepare a synthetic hydrocolloid include hydroxyalkyl acrylates and methacrylates, (such as 2-hydroxyethyl acrylate, 2-hydroxyethyl methacrylate, 2-hydroxypropyl acrylate, 2-hydroxypropyl methacrylate, 2,3-dihydroxypropyl methacrylate), acrylic acid, methacrylic acid and a tertiary amino-methacrylimide, (e.g. trimethylamino-methacrylimide), crotonic acid, and pyridine.

Other monomers useful to prepare a synthetic hydrocolloid include water soluble amides, (such as N-(hydroxymethyl)acrylamide and -methacrylamide, N-(3-hydroxpropyl)acrylamide, N-(2-hydroxyethyl) methacrylamide, N-(1,1-dimethyl-3-oxabutyl)acrylamide N-[2-(dimethylamine)ethyl]acrylamide and -methacrylamide, N-[3-(dimethylamino)-2-hydroxylpropyl]methacrylamide, and N-[1,1-dimethyl-2-(hydroxymethyl)-3-oxabutyl]acrylamide); water-soluble hydrazine derivatives, (such as trialkylamine methacrylimide, and dimethyl-(2-hydroxypropyl)amine methacrylimide); mono-olefinic sulfonic acids and their salts, (such as sodium ethylene sulfonate, sodium styrene sulfonate and 2-acrylamideo-2-methylpropanesulfonic acid); and the following monomers containing nitrogen in the non-cyclic or cyclic backbone of the monomer: 1-vinyl-imidazole, 1-vinyl-indole, 2-vinyl imidazole, 4(5)-vinyl-imidazole, 2-vinyl-1 -methyl-imidazole, 5-vinyl-pyrazoline, 3-methyl-5-isopropenyl-pyrazole, 5-methylene-hydantoin, 3-vinyl-2-oxazolidone, 3-methacrylyl-2-oxazolidone, 3-methacrylyl-5-methyl-2-oxazolidone, 3-vinyl-5-methyl-2-oxazolidone, 2- and 4-vinyl-pyridine, 5-vinyl-2-methyl-pyridine, 2-vinyl-pyridine-1-oxide, 3-isopropenyl-pyridine, 2- and 4-vinyl-piperidine, 2- and 4-vinyl-quinoline, 2,4-dimethyl-6-vinyl-s-triazine, and 4-acrylyl-morpholine.

Other hydrocolloidal polymers, either naturally occurring or synthetically prepared, are useful in the present invention. These materials include polyvinyl alcohol, polyoxyalkylenes, and such naturally occurring or synthetically modified hydrocolloidal materials as polysaccharides, gums, and modified cellulosics.

Representative polysaccarides include starch, glycogen, hemicelluloses, pentosans, gelatin, celluloses, pectin, chitosan, and chitin. Representative gums include Arabic, Locust Bean, Guar, Agar, Carrageenan, xanthan, Karaya, alginates, tragacanth, Ghatti, and Furcelleran gums. Representative modified celluloses include methyl cellulose, hydroxypropyl methyl cellulose, carboxymethylcellulose, and hydroxypropyl cellulose.

Crosslinking of the linear polymer chains of the hydrocolloid may be desired to improve cohesive properties of the gel dispersed in the pressure sensitive adhesive matrix. When such crosslinking is desired for polymers made from vinyl monomers discussed above, a multi-ethylenically unsaturated compound with the ethylenic groups being vinyl, allyl, or methallyl groups bonded to nitrogen, oxygen or carbon atoms can be used.

Non-limiting examples of crosslinking agents for vinyl containing polymers include divinyl, diallyl, or dimethallyl esters (e.g. ethylene glycol dimethacrylate, divinyl succinate, divinyl adipate, divinyl maleate, divinyl oxalate, divinyl malonate, divinyl glutarate, diallyl itaconate, diallyl maleate, diallyl fumarate, diallyl diglycolate, diallyl oxalate, diallyl adipate, diallyl succinate, diallyl azelate, diallyl malonate, diallyl glutarate, dimethallyl maleate, dimethallyl oxalate, dimethallyl malonate, dimethallyl succinate, dimethallyl glutarate, and dimethallyl adipate); divinyl, diallyl or dimethallyl ethers (e.g. diethyleneglycol divinyl ether, butane diol divinyl ether, ethylene glycol divinyl ether, ethylene glycol diallyl ether, diethylene glycol diallyl ether, butane diol diallyl ether, ethylene glycol dimethallyl ether, diethylene glycol dimethallyl ether, and butane diol dimethallyl ether); divinyl, diallyl or dimethallyl amides including bis(N-vinyl lactams), (e.g., 3,3'-ethylene bis(N-vinyl-2-pyrrolidone) and methylene-bis-acrylamide); and divinyl, diallyl and dimethallyl ureas.

Preferable crosslinking agents include ethylene glycol dimethacrylate, methylene-bis-acrylamide, diallyl maleate, and 3,3'-ethylidene bis (N-vinyl-2-pyrrolidone).

For n-vinyl lactams, the preferred crosslinking agents are diallyl maleate and 3,3'-ethylidene bis (N-vinyl-2-pyrrolidone).

For acrylates and methacrylates, the preferred crosslinking agents are ethylene glycol dimethacrylate and methylene-bis-acrylamide.

Preferred hydrocolloids for the present invention are linear or crosslinked polyvinyl lactams. Of the polyvinyl lactams, N-vinyl-2-pyrrolidone is preferred.

When crosslinking is desired, such crosslinking agents as diallyl maleate or 3,3'-ethylidene bis (N-vinyl-2-pyrrolidone) may be used to crosslink such polyvinyl lactams generally and poly-N-vinylpyrrolidone particularly.

Preferably, the crosslinked hydrocolloid is poly-N-vinylpyrrolidone prepared from the reaction of from about 97 to about 99.92 percent by weight of N-vinyl-2-pyrrolidone and from about 0.08 to about 3 percent by weight of 3,3'-ethylene bis N-vinyl-2-pyrrolidone. Most preferably, the 3,3'-ethylene bis N-vinyl-2-pyrrolidone comprises about 0.16 percent by weight of the poly-N-vinylpyrrolidone.

THE SWELLING AGENT

The swelling agent for the hydrocolloid may be a broad variety of liquids which are non-volatile or non-evaporative in ambient climatic conditions, and which are also incompatible with or extremely insoluble in the pressure sensitive adhesive or its solvent(s). The swelling agent must also be capable of swelling the hydrocolloid chosen, in order to form the gel phase of the composite of the present invention.

Non-volatility avoids evaporative loss of the swelling agent from the gel, thereby retaining the gel's moisture vapor transmission utility for continued periods. Non-volatility for the swelling agent is desired not only at room or body temperatures but also at the elevated temperatures of processing which range from about 75° C. to about 250° C. Because these non-volatile swelling agents have humectant properties at room temperatures, it is better to characterize an acceptable minimum amount of non-volatility at elevated temperature. For example, acceptable swelling agents for the present invention are sufficiently non-volatile if less than 10 percent of a given volume evaporates after exposure to a temperature of 75° C. for one hour.

Incompatibility avoids plasticization of the pressure sensitive adhesive by the swelling agent. No significant migration of the swelling agent into the pressure sensitive adhesive occurs because of their relative mutual insolvency. When the swelling agent is hydrophilic and the pressure sensitive adhesive preferably is hydrophobic, there is a continuous and strong tendency for phase separation.

Because the swelling agent is incompatible with the pressure sensitive adhesive, there is no significant migration of the swelling agent liquid from the gel phase into the adhesive matrix. A swelling agent compatible with the pressure sensitive adhesive would undesirably plasticize the adhesive, destroying its effectiveness as a skin adhesive.

Optimally, no swelling agent should migrate from the gel to the pressure sensitive adhesive matrix. Plasticization of the pressure sensitive adhesive is avoided if less than about 5 weight percent of swelling agent migrates into the pressure sensitive adhesive matrix. However, in no event should the weight fraction ratio of hydrocolloid to swelling agent exceed 3:1. Thus, depending on the weight fraction ratio of pressure sensitive adhesive to gel, up to about 5 weight percent of swelling agent can migrate into the pressure sensitive adhesive without harming the properties of the gel or the adhesive of the composite. But less than 2 weight percent is acceptable in most instances, with less than than 1 weight percent being desirable and less than 0.5 weight percent being preferred.

Varieties of non-volatile swelling agents within the scope of invention, which are incompatible with the pressure sensitive adhesives contemplated herein, include room temperature liquid polyols, (including polyhydric alcohols), such as glycerol, propylene glycol, poly(ethylene) glycol (having a molecular weight in the range of about 200 to about 600) and polypropylene glycol (having a molecular weight in the range of about 350 to about 1,000); room temperature solid polyols (including polyhydric alcohols), (such as sorbitol, erythritol, threitol, ribotol, arabinitol, xylitol, allitol, talitol, mannitol, glucitol, glactitol, iditol, pentaerythritol, heptitol, octitol, nonitol, decitol, and dodecitol), blended with a room temperature liquid polyol; monoanhydroalditols (such as styracitol, polyalitol, D-Fructose, 1,4 anhydro D-mannitol and 1,4 anhydro-D-glucitol) blended with a room temperature liquid polyol; monosaccharides (such as pentoses, hexoses, and heptoses) blended with a room temperature liquid polyol; and ether alcohols, such as poly(ethylene) glycol ether (having a molecular weight in the range of 600 to 20,000) and polypropylene glycol ether (having a molecular weight in the range of 1,000 to 5,000) blended with a room temperature liquid polyol.

Of these polyols, desirable swelling agents are glycerol, propylene glycol, polyethylene glycol (200–600 molecular weight) and sorbitol blended with glycerol. Because of its non-volatility and low-cost availability, glycerol is the preferred swelling agent.

Optionally, volatile solvents such as water and monohydric alcohols may be used to assist in the preparation of the gel by initiating the swelling of the hydrocolloids or in aiding the dispersion of the gel particles in a hydrophobic pressure sensitive adhesive matrix. Whether in a hydrophobic solution or in a suspension or emulsion, such processing volatile agents are not considered swelling agents of the present invention. The extent of removal of these volatile solvents is dependant on the requirements of the product application. In addition, depending on the air tightness of the packaging of a product incorporating a composite of the present invention, the gel particles therein may absorb atmospheric moisture. This may also be more or less desirable again depending on the product application.

INTERRELATED WEIGHT FRACTIONS OF GEL AND ADHESIVE AND WEIGHT FRACTION RATIO OF HYDROCOLLOID TO SWELLING AGENT

To achieve a balance of pressure sensitive adhesive properties and gel properties, the weight fractions of gel and adhesive in the resulting composite are controlled. However, because of the broad scope of properties which may be balanced, the gel may be dispersed in an amount by weight of about 1 to 95 percent by weight of the combined weight of gel and adhesive in the composite.

To achieve the proper gel properties in view of the weight fractions of the gel and the adhesive, the weight fractions of the hydrocolloid and the swelling agent are controlled using weight fraction ratios for them.

The pressure sensitive adhesive may have a weight fraction of from about 5 to about 99 percent by weight of the gel-adhesive composite. Desirably, the weight fraction of the adhesive in the gel-adhesive composite ranges from about 20 to about 95 percent by weight. Preferably, the weight fraction of the pressure sensitive adhesive in the gel-adhesive composite is from about 25 to about 90 parts by weight.

The hydrocolloid may have a weight fraction of from about 0.01 percent to about 72 percent of the gel-adhesive composite of the present invention. Desirably, the weight fraction of the hydrocolloid in the gel-adhesive composite ranges from about 0.05 to about 48 percent. Preferably, the weight fraction of the hydrocolloid in the gel-adhesive composite ranges from about 0.50 to about 30 weight percent.

The swelling agent may have a weight fraction of from about 0.25 to about 95 percent by weight of the gel-adhesive composite. Desirably, the range of the weight fraction of the swelling agent in the composite depends on the weight fraction of the hydrocolloid in the composite.

Depending on the properties desired for the gel-adhesive composite, the range of weight fraction ratios for the hydrocolloid to the swelling agent can be from about 3:1 to about 1:99. At the ratio of about 3:1, there is sufficient swelling agent to achieve a soft and pliable gel suitable for maintaining the strong adhesiveness of the composite. At the ratio of about 1:99, there is sufficient hydrocolloid to prevent the swelling agent from migrating through the pressure sensitive adhesive and "blooming" to the surface of the composition, thereby destroying its adhesiveness.

Desirably, the ratio of weight fractions of the hydrocolloid to the swelling agent is from about 1.5:1 to about 1:19. Preferably, based on a balancing of the performance of the moisture vapor transmission rate of the gel with the adhesiveness of the adhesive in the composite, the ratio of the weight fractions of the hydrocolloid to the swelling agent is from about 1:1.5 to about 1:19.

FIG. 2, a tri-coordinate graph, provides a convenient depiction of the acceptable, desirable and preferable weight fraction ratios of the three necessary components of the gel-adhesive composite of the present invention. FIG. 2 also depicts the ranges of acceptable, desirable and preferable weight fraction ratios of the hydrocolloid and the swelling agent within the gel of the present invention.

The area in FIG. 2 inside lines A, $A^1$, and $A^2$ graphically depicts that the weight fraction of the pressure sensitive adhesive is from about 5 to about 99 percent, the weight fraction of the hydrocolloid is from about 0.01 to about 72 percent, and the weight fraction of the swelling agent is from about 0.25 to about 94 percent as adjusted for the ratios of the hydrocolloid to the swelling agent of from about 3:1 to about 1:99 (the slopes of the lines A and $A^2$, respectively).

For example, a composite containing 20 percent by weight of the pressure sensitive adhesive, 60 percent by weight of the hydrocolloid, and 20 percent by weight of the swelling agent appears on line A and hence at the border of the acceptable area, where the ratio of the hydrocolloid to the swelling agent is 3:1. For example, a composite having 50 percent by weight of the pressure sensitive adhesive, about 1 percent by weight of the hydrocolloid, and about 49 percent by weight of the swelling agent is on line $A^2$ within the acceptable area, where the ratio of the hydrocolloid to the swelling agent is about 1:99.

A weight fraction of 60 percent for the pressure sensitive adhesive, 20 percent by weight of the hydrocolloid, and 20 percent by weight of the swelling agent yields a composite clearly within the area in FIG. 2 bounded by lines A, $A^1$, $A^2$ where the ratio of the hydrocolloid to the swelling agent is 1:1.

The areas bounded by bordering lines B, $B^1$, $B^2$ and $B^3$ and C, $C^1$, $C^2$ and $C^3$ in FIG. 2 similarly identify the desirable and preferable weight fractions of the composites of the present invention, respectively. The example in the prior paragraph of the weight percent pressure sensitive adhesive:hydrocolloid:swelling agent ratio of 60:20:20 is also within the desired range of weight fractions bounded by lines $B-B^1-B^2-B^3$, where the desired ratio of hydrocolloid to swelling agent of 1:1. But an adhesive:hydrocolloid:swelling agent ratio of 50:10:40 is only within the preferred area of weight percent ranges bounded by lines $C-C^1-C^2-C^3$, where the ratio of hydrocolloid to swelling agent is 1:4.

The bordering lines also demonstrate the desired and preferred hydrocolloid:swelling agent ratios. Line $B^1$ has a slope matching the hydrocolloid:swelling agent ratio of 1.5:1. Line $B^3$ has a slope matching the ratio of 1:19. Line $C^1$ has a slope matching the ratio of 1:1.5. Shorter Line $C^3$ has the same slope as the slope of longer Line $B^3$, 1:19.

As stated previously, optimally no swelling agent in the gel should migrate into the adhesive matrix. Preferably less than 0.5 weight percent, and desirably less than 1 weight percent, of the adhesive matrix should comprise migrated swelling agent.

In no event should the amount of swelling agent remaining in the gel cause the hydrocolloid:swelling agent ratio to exceed about 3:1.

Further, in no event should the amount of swelling agent migrating into the adhesive matrix exceed 5 weight percent of the adhesive. This avoids plasticization of the adhesive and reduction of adhesive strength. Residuing of adhesive on the skin is also avoided.

The above constraints define the outer limits of tolerance of swelling agent migration. It is desirable to select swelling agents and pressure sensitive adhesives which are incompatible, to avoid reaching such outer limits. Such incompatibility of swelling agent and adhesive preserves the softness and moisture vapor transmission rate properties of the gel particles dispersed within the adhesive matrix for composites of all ratios of the present invention.

OPTIONAL COMPONENTS

The addition of a variety of biologically active materials into the gel-adhesive composite of the present invention is desirable when the composite is placed in contact with the skin or skin opening of a patient. Bandages, tapes, dressings, drapes, and the like are all used in conditions where it is desirable to reduce bacteria levels to minimize infection risk or to treat the effects of infections at the skin or skin openings of a patient. For example, in the application of composites of the present invention as incise drapes, antimicrobial agents may be incorporated into the gel of the composition. Broad spectrum antimicrobial agents are disclosed in U.S. Pat. No. 4,310,509, which disclosure is incorporated by reference.

Useful antimicrobial agents include a wide variety of agents which are compatible with both the gel and the pressure sensitive adhesive of the composite. These agents can be incorporated prior to polymerization or gelation of the hydrocolloid, provided they do not interfere with such reaction(s). Alternatively, the agents can be incorporated after polymerization of the hydrocolloid, if any. In the latter case, the antimicrobial agents are dissolved or dispersed in either non-volatile swelling agent or volatile solvent.

Examples of antimicrobial agents are numerous, but desirably such antimicrobial agents as parachlorometaxylenol; chlorhexidine and its salts such as chlorhexidine acetate and chlorhexidine gluconate; iodine; iodophors; poly-N-vinylpyrrolidone-iodophors; silver oxide, and silver and its salts, and antibiotics (e.g., neomycin, bacitracin, and polymyxin B) are useful in accordance with the present invention.

The antimicrobial agents may be included in the composites in a weight from about 0.01 percent to about 10 percent by weight of the total composite after the weight percents of the adhesive, hydrocolloid and swelling agent are determined.

Other additives may be incorporated into the composite to enhance the physical properties of the adhesive and the antimicrobial properties of the composite containing an antimicrobial agent. For example, iodates and iodides may be added to enhance the solubility of the iodine antimicrobial agent during the introduction of the antimicrobial agent into the gel and to adjust the free iodine in the composite.

Photoinitiators, and other catalysts may be used in the polymerization processes for the pressure sensitive adhesive and in the polymerization or gelation of the hydrocolloid.

Compounds to buffer the pH of the composite may be added to provide a non-irritating pH for use with sensitive skin tissue or to otherwise maximize antimicrobial activity.

Further, the incorporation of a surfactant into the composite may improve antimicrobial activity in or at the skin of the patient.

PREPARATION OF THE GEL-ADHESIVE COMPOSITE

There are two methods currently known for the preparation of the composite of the present invention. Both methods involve the separate preparation of the pressure sensitive adhesive and the gel following by the mixing and drying of them to form the composite.

One method involves mixing the gel either with or without a hydrophilic solvent into an adhesive in bulk or in a volatile solvent. The other method involves mixing the gel into a latex adhesive with volatile hydrophilic solvent or solvents.

When the method used involves gel particles mixed into an adhesive in bulk or in a volatile, hydrophobic solvent, the gel particles must be dispersed into the adhesive. Equipment such as a "Laboratory Dispersator, Series 2000, Model 84" mixer, commercially available from Premier Mill Corporation of Reading, Pa. may be used for solution preparation. A Banbury mixer could be used for bulk preparation. The process of mixing should continue until the gel particles are fully dispersed in the adhesive. Then, the mixing is stopped to allow for the removal of any bubbles created during the mixing process. The mixing process may occur at ambient temperatures and pressures.

When the composite is prepared by mixing the gel particles into a latex solution of the hydrophobic pressure sensitive adhesive, the mixing may be accomplished by using the "Laboratory Dispersetot" mixer described above. The mixing process may occur at ambient temperatures and pressures. The mixing should continue until the gel particles are fully dispersed. Then the mixing is stopped to allow for the removal of any bubbles created during the mixing process.

Regardless of the method of preparation, whenever a volatile solvent for the pressure sensitive adhesive, the gel, or both is present during the final mixing, it/they must be removed, generally by application of heat or other drying mechanism. As drying occurs, the adhesive forms a nearly continuous matrix with the gel particles dispersed therein. The temperatures of evaporating the volatile solvent(s) without adversely affecting the remaining adhesive and gel depends upon the type of volatile solvent(s) employed. Generally, however, the mixture is dried at temperatures between about 75° C. and about 250° C.

The resulting composite may be spread or coated onto a release liner and dried to form films having thicknesses of from about 10 to about 1,000 microns and desirably from about 20 to about 100 microns. Thereafter, depending on the desired application, the layer of composite may be applied to a backing material by laminating.

In elevated temperature preparations, the composite can endure temperatures in excess of 100° C. without chemical or physical deterioration. If a biologically active material such as an antimicrobial agent is included in the composite, the temperature of the drying of the composite and its lamination to a backing material should not exceed 100° C.

PREPARATION OF THE PRESSURE SENSITIVE ADHESIVE

The preparation of the pressure sensitive adhesive depends on the type of adhesive, the type of polymerization (e.g., addition or condensation), and the polymerization technique (e.g., bulk, solution, suspension or emulsion polymerization).

The pressure sensitive adhesive polymerization technique chosen is selected from conventional polymerization technique(s) known for a particular pressure sensitive adhesive. Sources of polymerization preparation techniques include *Organic Polymer Chemistry*, K. J. Saunders, Chapman and Hall (Halsted Publishing, New York, 1973), *Applied Polymer Science*, R. W. Tess and G. W. Poehlein, American Chemical Society (American Chemical Society, Washington, D.C., 1981), and *Principle of Polymerization*, George Odien, Wiley-Interscience (John Wiley and Sons, New York, 1981), and the *Handbook of Pressure Sensitive Adhesive Technology, 2nd Ed.*, supra, all of which are incorporated herein by reference.

For example, acrylic pressure sensitive adhesives may be prepared according to U.S. Pat. No. Re: 24,906. When prepared by solution polymerization, the monomers are soluble in solvents, commonly ethyl acetate, cyclohexane, toluene, and n-heptane. The polymer is also usually soluble in the solvent allowing a pure polymer to be coated onto a surface and then dried. When prepared by emulsion polymerization, the latex of water-insoluble polymers in water maintains a phase separation until removal of the water.

Pressure sensitive adhesives may be prepared by solution polymerization from A-B-A block copolymers, natural rubber, styrene-butadiene, polyisoprene, butyl rubber, polyisobutylene, polychloroprene, and blends thereof. Pellets of the commercially available polymer are mixed into a solvent and heated in the presence of tackifiers and often plasticizers, in order to develop a non-rigid polymer having the requisite tack. Chapters 11, 13, 14, and 19 of the *Handbook of Pressure Sensitive Adhesive Technology 2nd Ed.*, referenced above, discusses the choices of materials and methods of preparation. A frequently used tackifier is polyterpene resin.

The rubber based adhesives may also be prepared in a latex. For example, styrene and butadiene may be dispersed in water with an emulsifier (such as sodium alkyl benzene sulfonate) and an initiator (such as potassium persulfate). Polymerization occurs typically anaerobically with mixing for about 16–24 hours at 60° C. Chapter 12 of the *Handbook of Pressure Sensitive Adhesive Technology 2nd Ed.*, supra, describes such latex preparation processes.

Silicone pressure sensitive adhesives are usually commercially supplied in a hydrocarbon solvent. Upon evaporation, the silicones exhibit pressure sensitive adhesive properties. As described in Chapter 18 of the *Handbook of Pressure Sensitive Adhesive Technology 2nd Ed.*, supra, a catalyst (such as an organic peroxide, an amino silane, or a metal salt of an organic acid) is added to reinforce the silicone network, increasing cohesiveness.

The polymerization of vinyl ether homopolymers may be carried out by batch processing, or continuous processing in bulk or in solution. Whichever processing is used, cationic initiators such as $BF_3$ or $AlCl_3$ are present. Copolymers of vinyl ethers and acrylates are polymerized by free radical emulsion polymerization in water with potassium peroxodisulfate. Chapter 17 of the *Handbook of Pressure Sensitive Adhesive Technology 2nd Ed.*, supra, describes the polymerization.

If volatile solvents are necessary or desirable for the preparation of the pressure sensitive adhesive, such solvents should be hydrophobic and generate phase separating regions when encountering the gel particles having hydrophilic swelling agents therein or volatile hydrophilic solvents used to prepared the gel. Desirably, hydrophobic volatile solvents for the pressure sensitive adhesive are aliphatic or aromatic hydrocarbons, such as heptane, toluene, xylene, and the like and blends containing other miscible solvents such as ethyl acetate.

PREPARATION OF THE GEL

The preparation of the gel involves the mixing or swelling of finely divided particles of the hydrocolloid with the swelling agent and optionally a volatile solvent or solvents compatible or miscible with the swelling agent but incompatible with the adhesive.

The preparation of the gel occurs after preparation of the hydrocolloid and its separation into finely divided particles. A swelling agent is then added in amounts sufficient to achieve the desired weight fraction ratio. The swelling agent swells the hydrocolloid prior to any mixing with the adhesive, such that the swollen gel particles are fully formed prior to being dispersed in the pressure sensitive adhesive matrix.

Swelling may occur at ambient or elevated temperatures (up to 100° C.) and ambient pressures in a mixing vessel with simple hand mixing or stirring. The swelling may occur in the presence of such volatile, hydrophilic solvents as water, ethanol, methanol and other monohydric alcohols. However, to the extent possible, it is desirable to swell the hydrocolloid without volatile solvents to avoid the subsequent efforts to remove the solvent to form the composite.

PREPARATION OF THE HYDROCOLLOID

The preparation of the hydrocolloid depends on the choice of hydrocolloid used. If the hydrocolloid is naturally occurring then it is used directly. If the hydrocolloid is synthetic or synthetically modified from a naturally occurring material, the synthesis may be by a variety of methods including condensation polymerization or addition polymerization from monomeric units. The choice of hydrocolloid polymerization technique may be selected based on the hydrocolloid in reference to conventional polymerization technique(s) known for that hydrocolloid. Sources of polymerization preparation techniques include *Organic Polymer Chemistry*, K. J. Saunders, Chapman and Hall, *Applied Polymer Science*, R. W. Tess and G. W. Poehlein, American Chemical Society, and *Principles of Polymerization*, George Odien, Wiley-Interscience, supra.

Desirably, a free radically polymerized hydrocolloid is prepared by photochemically activated polymerization. The monomer, desirably also a crosslinking agent, and the photoinitiator can be polymerized in bulk or in a hydrophilic solution of the swelling agent alone or with other hydrophilic solvents which may be volatile. The precursor can be coated on a flat surface and irradiated with ultra-violet light. Optionally, the hydrocolloid can be ground into particles, emulsified in a volatile solvent and reprecipitated to remove any unreacted monomer, and then dried and ground into a fine powder.

Photoinitiators available for use are well known and have been described in the polymerization art, e.g., Chapter II of "Photochemistry" by Calvert and Pitts, John Wiley and Sons (1966) and in Progress in organic Coatings, 13 (1985) 123–150, both disclosures of which are incorporated herein by reference. Representative examples of such initiators include acyloins and related compounds such benzoin, benzoin methyl ether, benzoin ethyl ether, benzoin isopropyl ether, benzoin isobutyl ether, alpha-methylbenzoin, and 2-hydroxy-2-methyl-1-phenyl-1-propanone; and benzilketals such as benzildimethylketal and benzildiethylketal. A presently preferred photoinitiator is 2-hydroxy-2-methyl-1-phenyl-1-propanone.

Generally, the photoinitiator is used in amounts ranging from about 0.01 to about 5 percent by weight of monomer. Preferably, about 0.02 to 2 percent by weight of photoinitiator is used. When the activating energy is ultraviolet light, the irradiation is typically initiated at a temperature in the range of 0° C. to 50° C. for 0.5 minutes to 5 hours or more depending upon the intensity of the radiation.

When poly N-vinylpyrrolidone is the hydrocolloid chosen, polymerization may take place in solution, bulk, or suspension. When N-vinyl-2-pyrrolidone is polymerized in a hydrophilic solution of a solvent and/or the swelling agent, the solids achieved are swollen gel particles which may be ground into fine particles. Desirably, the swelling agent may serve as the solvent.

When the polymerization of N-vinyl-2-pyrrolidone is in bulk, a hard polymer is obtained which must also be ground into fine particles prior to swelling such particles with the swelling agent.

However obtained, the hydrocolloid particles are swollen with the swelling agent to yield soft and pliable gel particles. As described above, the swollen gel particles are dispersed into the adhesive solution using a high shear grinder or mixer to physically randomly disperse the gel particles of various dimensions into the pressure sensitive adhesive matrix.

USEFULNESS OF THE GEL-ADHESIVE COMPOSITE

Figure 1:
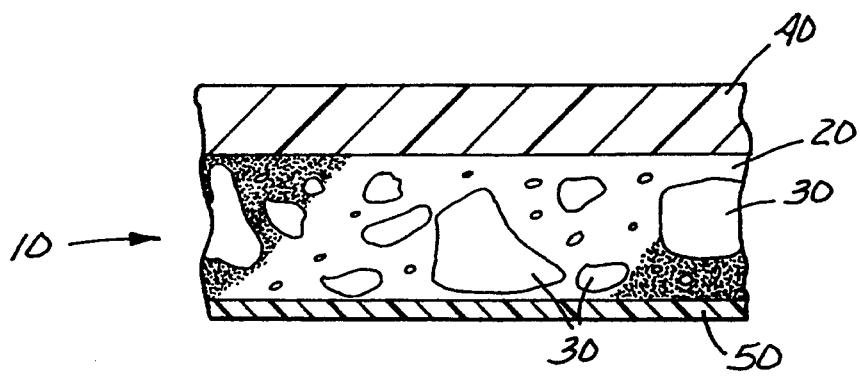
FIG. 1 is a cross-section of a typical coating of the gel-adhesive composite of the present invention on a backing material, showing in the coating the dispersion of the gel throughout the pressure sensitive adhesive matrix.

Referring to FIG. 1, the usefulness of the composite may be seen. The gel-adhesive layer 10 comprises a plurality of discrete gel particles 30 dispersed in the continuous matrix of the pressure sensitive adhesive 20. The layer 10 is contacting both a layer 40 of backing material and a release liner 50.

The discrete gel particles 30 are of various sizes and are dispersed randomly in the adhesive 20. The variety of sizes depends on the size of the hydrocolloid particle prior to swelling and gel break-up during dispersive mixing or shearing. Desirably, the particles 30 range from about 1 micron to about 600 microns.

The composite of the present invention may be coated onto a variety of webs or backing materials 40, including films, substrates, or other elastic, porous or breathable woven or nonwoven materials useful in medical applications. A release liner 50, typically a silicone release liner, protects the other exposed surface of the coated layer 10.

In such manner, the release liner 50 is removed and the layer 10 of composite may be applied to the skin of the patient as a part of a medical tape, a surgical drape, an incise drape, a wound dressing, a bandage of general medicinal utility, or other medical device. The adhesiveness of the pressure sensitive adhesive combined and balanced with the high moisture vapor transmission rate properties of the gel permits wide utility in medical applications.

The composite layer 10 may be coated on a layer 40 of any of several backing materials also having a high moisture vapor transmission rate for use as medical tapes, dressings, drapes, bandages, and the like. Suitable backing materials include those disclosed in U.S. Pat. Nos. 3,645,835 and 4,595,001, the disclosures of which are incorporated by reference. Other examples of a variety of films commercially available as extrudable polymers include "Hytrel$^R$ 4056" and "Hytrel$^R$ 3548" branded polyester elastomers available from E. I. DuPont de Nemours and Company of Wilmington, Del., "Estane" branded polyurethanes available from B. F. Goodrich of Cleveland, Ohio or "Q-thane" branded polyurethanes available from K. J. Quinn & Co. of Malden, Mass.

The layer 10 combined with a layer 40 of suitable backing material may be used as a surgical drape, and particularly an incise drape. Suitable backing materials are disclosed in U.S. Pat. Nos. 4,627,427 or 3,809,077, the disclosures of which are incorporated by reference., to be used for incise drapes or surgical drapes, respectively.

When used as an incise drape, the composite may be used with a film prepared from "Hytrel 4056" branded polyester elastomer available from DuPont as the backing material.

The composite layer 10 can be coated on the backing layer 40 by a variety of processes, including, direct coating, lamination, and hot lamination. The backing layer 40 may also be a release liner onto which the composite is coated prior to drying.

The method of applying the composite to the release liner involves the same coating process as that described above for the preparation of the composite after the drying step. The methods of lamination and hot lamination involve the application of pressure, or heat and pressure, respectively, on the layer of composite layer 10 to the backing material layer 40. The temperature for hot lamination ranges from about 50° C. to about 250° C., and the pressures applied to both lamination and hot lamination range from 0.1 Kg/cm$^2$ to about 50 Kg/cm$^2$.

The balance of adhesive and moisture vapor transmission properties desired can depend on the climatic conditions where the composite may be used. Diaphoretic patients or patients in intemperate climates where perspiration is unwanted but constantly present may use composites which emphasize high moisture vapor transmission rates over the adhesiveness of the tape, bandage, or dressing used. Conversely, in temperate climates or even in the chilled conditions of modern operating rooms, the composites which emphasize strong adhesives for use as incise drapes and which have near transparency and continuously good moisture vapor transmission of body fluids are needed.

High moisture vapor transmission rates of the composite encourage a rate of moisture withdrawal from the surface of the skin which thereby attempts to maintain dry skin conditions under the tape, dressing, drape and the like. The adhesive matrix thus remains adhered. In addition to maintaining continued good adhesion, low skin or wound moisture levels reduce the risk of infection.

As described above, optionally, the composite may contain an antimicrobial agent in gel-adhesive layer 10 help reduce infection at the skin or skin opening.

While FIG. 1 and various examples appearing below have described the use of the composite with a backing web or substrate, the scope of the invention is not so limited. There are circumstances where a backing layer would not be desired and the adhesive would be used as a coating alone on the skin or skin opening. Examples of uses of the coating alone include the use of the composite to hold two pieces of skin tissue together or the composite to hold a liquid absorbing material, such as gauze, in contact with the skin.

While the composites of the present invention have particular utility in the medical or veterinary applications, the utility of the composites is not so limited. A wide variety of adhesive composites having continuous moisture vapor transmission capability may be used for application to inanimate objects which must be kept dry notwithstanding a continuing exuding of moisture or water. The securement of a tape to repair torn material exposed to wet environments, such as a tent, may be aided by the use of the composite of the present invention because the moisture vapor transmission rate of the tape will attempt to provide continued dry stick adhesion.

PROPERTIES OF THE GEL-ADHESIVE COMPOSITE

Referring again to FIG. 1, the gel particles 30 dispersed in the continuous adhesive matrix 20 provide the means by which moisture at the skin is continuously removed by diffusion of moisture through the gel-adhesive layer 10.

While not being bound to any particular theory, it is believed that the swelling of the hydrocolloid with the non-volatile swelling agent at weight fraction ratios from 3:1 to 1:99 prior to mixing of the gel with the adhesive provides a high diffusion rate environment for moisture and antimicrobial to rapidly diffuse through the gel. By comparison, the hard, unswollen hydrocolloid particles in stoma-type adhesives have very low diffusion rates and require swelling of the hydrocolloid by moisture prior to providing high moisture or antimicrobial agent diffusion through that type of adhesive.

Thus, the gel particles 30 more quickly and more efficiently transport the moisture from the skin because the gel particles 30 are already in a swollen equilibrium before any contact with the wet or moist environment of the skin. Because the swelling agent is non-volatile, the equilibrium is maintained both before the composite is used and during use in contact with skin. The volatile moisture is transmitted, not the non-volatile swelling agent. These particles 30 attempt to continuously dry an otherwise wet environment by the transmission of moisture from the skin or the skin opening while the adhesive matrix 20 maintains adhesion.

In addition to the interrelated weight fractions of the pressure sensitive adhesive, the hydrocolloid, and the swelling agent and the ratio of the hydrocolloid to the swelling agent, it is important for the present invention to have gel particles 30 in the composite 10 which are very soft and pliable. If the particles 30 are not soft and pliable, the particles begin to become reinforcing materials in the adhesive matrix 20, stiffening the gel-adhesive composite layer 10 and diminishing the composition's adhesiveness.

The soft and pliable gel particles 30 permit the adhesive matrix 20 of the gel-adhesive composite layer 10 to continue to adhere to the skin in those regions where the gel particles 30 do not contact the skin.

Shear modulus is a measurement of the softness and pliability desired for the gel of the present invention. Generally the shear modulus of the gel particles 30 should be less than $6.2 \times 10^6$ dynes/cm$^2$.

A desirable upper limit for the shear modulus of the gel of the present invention is $1.5 \times 10^5$ dynes/cm$^2$. A more preferred maximum of shear modulus for the gels of the composites of the present invention is $4.2 \times 10^4$ dynes/cm$^2$.

As is known to those skilled in the art, the shear modulus upper limit of $6.2 \times 10^6$ dynes/cm$^2$ represents an extremely soft material compared with other elastomers known to those skilled in the art.

The balance of the high moisture vapor transmission rate and the continued adhesive properties for that composite are also influenced by the particle size of the gel particles 30 in the adhesive matrix 20. It is axiomatic that smaller particles offer a larger surface area to volume ratio, which helps increase moisture vapor transmission. But it has also been noted that particle sizes for the gel which approximate the thickness of layer gel-adhesive composite 10 of the composite are believed to act as a pore in the matrix of the adhesive, thereby also increasing the moisture vapor transmission rate.

Thus, a wide range of particle sizes may yield acceptable gel-adhesive composite results. A range of particle size for the gel particles 30 of from about 1 to about 600 microns is acceptable, while a range of particle size of from about 25 to about 100 microns is desirable.

The gel particles 30, soft, in swollen equilibrium and of various sizes dispersed in the adhesive matrix 20, can provide to the layer 10 a significantly higher moisture vapor transmission rate than the same adhesive without a gel dispersed therein. The amount of increase depends on the amount of gel dispersed in the adhesive matrix and the size of the gel particles so dispersed. One may increase the moisture vapor transmission rate property of an adhesive by dispersing gel particles therein. Also, one may improve adhesion with a thicker adhesive layer in a medical article while maintaining the moisture vapor transmission rate property of the original thickness of adhesive by dispersing gel into the thicker adhesive matrix. Thus, the moisture vapor transmission rate properties of a gel-adhesive composite of the present invention can be tailored to the use for the composite.

For example, it has been found with acrylate adhesives having as little as 10 weight percent of poly(N-vinyl lactam) particles swollen with glycerol, displays a 20 percent increase in the moisture vapor transmission rate. When there are substantial weight fractions of gel in the composite, for example, between 50 and 75 weight percent, the moisture vapor transmission rates can be as much as 200 to 700 percent greater than the pressure sensitive adhesive displays.

The high moisture vapor transmission rates achieved by the gel of the composite do not adversely impact the adhesion strength of the pressure sensitive adhesive. Initially, short term (a few hours), and long term (24 hours) adhesion values of the gel-adheisve composites having a broad range of gel concentrations follow the adhesion values of the pressure sensitive adhesive over the same periods. For example, in a preferred embodiment of poly (N-vinylpyrrolidone) hydrocolloid in glycerol swelling agent, the gel comprising 25 percent by weight of the composite, where the ratio of hydrocolloid to swelling agent was 1:1, the skin adhesion of the composite after 24 hours was nearly as great as the skin adhesion for the pressure sensitive adhesive alone after 24 hours.

Further, the gel-adhesive composites display excellent wet adhesion properties making the composite equally attractive to patient care conditions where dry skin environments become wet or where wet skin environments must be made drier.

The peel adhesive strength of the composites of the present invention are strong notwithstanding the presence or absence of humidity. For example, in a composite having about 75 percent by weight of an acrylate pressure sensitive adhesive and about 25 percent by weight of poly (N-vinyl lactam) gel, within which the lactam hydrocolloid to glycerol swelling agent ratio was about 0.43:1, the T-Peel adherence to low density polyethylene (LDPE) (which is used to simulate skin adhesion) at dry or humid conditions was better than the adhesiveness of the acrylate pressure sensitive adhesive alone. The humid LDPE test at 50 percent relative humidity shows a result which was even greater than the dry LDPE T-Peel adhesive strength.

Thus, the range of adhesive strength retained by the gel-adhesive composite may exceed the adhesive strength of the adhesive alone and at the very least ranges from about 40% to about 500% of the adhesive strength of the adhesive alone.

A useful feature of the gel-adhesive composites of the present invention is the apparent near transparency of the composite, notwithstanding the two phase nature of that composition. Because the gel and the pressure sensitive adhesive may be chosen from candidates having nearly identical indices of refraction, it is possible to achieve an at least nearly transparent composite. A nearly transparent composite enables the practitioner to use this coating as an adhesive for incise drapes or for other purposes which call for translucency approaching transparency. An incision area must be seen through the adhesive, and a composite of the present invention provides significantly improved utility over other adhesives.

While not being bound to any particular theory, it is believed that the near transparency of the composites of the present invention is directly related to the scattering of light caused by the dispersed gel particles 30 in the continous adhesive 20. The amount or degree of scattering is related to four physical properties: differences in indices of refraction of the various components in the composite, particle size of the gel particles, the weight fraction of the gel particles in the continuous adhesive, and the thickness of the composite.

The difference in the indices of refraction between the pressure sensitive adhesives and the gels of the composite may be as small as 10 percent. In the case of acrylate adhesives and gels of poly (N-vinyl lactams) swollen with glycerol the difference in indices of refraction may be as small as 5 percent, desirably as small as 2 percent and preferably as small as 1 percent to provide a nearly transparent composite.

Further, if the gel particles 30 are larger than the wavelengths of visible light, i.e., greater than 1 micron, then Rayleigh scattering can also be minimized.

Light scattering is also reduced by smaller weight fractions of the gel particles 30 in the adhesive 20, e.g., 30 percent versus 50 percent and the thinner coatings of layer 10 applied to the skin, e.g. 50 microns versus 100 microns. But these factors must be balanced against the need for strong adhesion and high moisture vapor transmission rate. Nonetheless, even with a weight fraction of gel particles 30 of as much as 95 weight percent dispersed in the adhesive 20 and coatings of the layer 10 of 100 microns thickness applied to the skin, the composites of the present invention can be nearly transparent.

While not intending to be an exhaustive treatment of the embodiments of the present invention, the following examples are illustrative of the scope of the invention which should not be limited thereto or thereby.

EXAMPLE 1

Crosslinked Poly (N-vinylpyrrolidone) Hydrocolloid Bulk Polymerization Using Photochemical Initiation A solution composed of 0.32 parts 3,3'-ethylidene bis (N-vinyl-2-pyrrolidone), 1.0 parts 2-hydroxy-2-methyl-1-phenyl-1-propanone (serving as the photoinitiator) and 100 parts N-vinyl-2-pyrrolidone were placed in a flat dish at a thickness of 1.3 centimeters and was irradiated through a 0.5 centimeter thick quartz plate with a "Sylvania$^R$ Sunlamp #052" from GTE Sylvania, Inc., Manchester, N.H., placed at a distance of 40 centimeters for about 20 minutes. The resultant crosslinked poly (N-vinylpyrrolidone) product was ground into a powder of particle size less than 0.25 centimeters using a blender and then thrice both emulsified in water and reprecipitated in acetone to remove residual monomers. The polymer was dried in a vacuum oven at 65° C. The polymer was then again ground into a fine powder using a commercially available grinder, a "Brinkmann Retsch Grinder" from Brinkmann Instruments Company, Westbury, N.Y. The grinder was used at 20,000 rpm outfitted with a 750 micron grate to provide a particle size distribution of 750 microns and smaller, with the majority (by weight percent) of particles between 25 and 200 microns in size. The hard hydrocolloid particles produced are available for swelling into the gel particles.

EXAMPLE 2

Pressure Sensitive Adhesive Solution Polymerization

This was the pressure sensitive adhesive (PSA) used as the continuous matrix. It did not contain any gel. For this example, it was an isooctyl acrylate/N-vinyl pyrrolidone copolymer (91/9% weight) dissolved at 25% weight solids in a solvent blend of 50/50 heptane/ethyl acetate.

100.1 grams of isooctyl acrylate, 0.88 grams of ethanol, 164.6 grams of heptane, 164.6 grams of ethyl acetate, 9.9 grams of N-vinyl-2-pyrrolidone, and 0.294 grams of azobisisobutyronitrile were charged to a one pint bottle. The bottle was flushed with a stream of nitrogen for 3-4 minutes, sealed, and tumbled in a water bath at 55° C. for 20 hours. The copolymer was formed and comprised 25% of the solution.

EXAMPLE 3

Gel of Swollen Hydrocolloid-Percent Weight Ratio of Hydrocolloid to Swelling Agent of 1:19

Ten parts of the hydrocolloid polymer described in Example 1 were mixed with 190 parts of glycerol. This mixture was placed in a blender and sheared to maintain the small particle size of the gels, around 25 to 200 microns, by reducing agglomeration of the gel particles. The gel particles were prepared for dispersing into the pressure sensitive adhesive.

EXAMPLE 4

Gel-Adhesive Composite with 10% Gel

To 50 parts of the pressure sensitive adhesive solution described in Example 2 was added 1.39 parts of gel of Example 3 and 2.09 parts of n-heptane and 2.09 parts of ethyl acetate. The mixture was mixed vigorously with a Laboratory Dispersator, Series 2000 model 84, commercially available from Premier Mill Corporation, Reading, Pa., for several minutes until the gel appeared evenly dispersed. The mixture was allowed to set one minute to allow bubbles to eliminate from the solution and the liquid was coated on a "Poly Slik S-8003" silicone release liner available from H. P. Smith at a thickness of 330 microns (13 mils). The coating was dried 15 minutes at room temperature conditions and then 15 minutes at 79° C. The dried adhesive was then laminated at a pressure of about 3.5 Kg/cm$^2$ to a segmented block polyester film, prepared from "Hytrel$^R$ 4056" polyester elastomer available commercially from DuPont de Nemours Company, Wilmington, Del. The film thickness was 28 microns.

EXAMPLE 5

Another Composite-25% Gel

To 50 parts of the adhesive solution described in Example 2 was added 4.17 parts of the gel particles of Example 3, 6.26 parts of n-heptane and 6.26 parts of ethyl acetate. The mixture was prepared, coated and laminated in accordance with Example 4.

EXAMPLE 6

Another Composite-50% Gel

To 50 parts of the adhesive solution described in Example 2 was added 12.50 parts of the gel particles of Example 3, 18.75 parts of n-heptane and 18.75 parts of ethyl acetate. The mixture was prepared, coated and laminated in accordance with Example 4.

EXAMPLE 7

Another Composite-75% Gel

To 30 parts of the adhesive solution described in Example 2 was added 22.50 parts of the gel particles of Example 3, 3.75 parts of n-heptane and 3.75 parts of ethyl acetate. The mixture was prepared, coated and laminated in accordance with Example 4.

The foregoing examples 4-7 illustrate the effect that the weight percent of gel, dispersed in an acrylic pressure sensitive adhesive, had on moisture vapor transmission rates (MVTR) of the composite. The results are shown in Table 1. The MVTR for each sample of the composite was determined using a variation of a ASTM method E96-80. The film was placed adhesive side down over the opening of a standard glass vessel half filled with deionized water. The MVTR was determined by first allowing the sample 24 hours to equilibrate to the test conditions of 39° C. and 20% ambient relative humidity and then measuring the weight loss in the following 24 hours. The results described in Table 1 demonstrate a dramatic increase in the MVTR of the laminate.

To more fully understand the actual improvement made to the composite over the use of adhesive alone, the MVTR for the composite was mathematically segregated. The following expression was used for calculating the MVTR of a two layer laminate of polymeric film and the composite.

1/MVTR (film) + 1/MVTR (composite) = 1/MVTR (laminate)

The MVTR of the film alone was also determined in order to solve the equation. Since the effect of higher coating weights will reduce the MVTR, the results have been normalized to the same coating weight in order for more meaningful comparisons to be made. These results demonstrate a very dramatic rise in MVTR by the various composites over the MVTR shown for the pressure sensitive adhesive alone.

TABLE I

| Example | Weight Fraction Ratio of PSA:Hydrocolloid: Swelling Agent | Coating Weight mg/cm$^2$ | Water Loss in 24.5 hr (g) | Laminate MVTR g/m$^2$/24 hr | Composite MVTR g/m$^2$/24 hr | Normalized Composite MVTR | % Increase in MVTR |
| --- | --- | --- | --- | --- | --- | --- | --- |
| 2 | 100:0:0 | 11.1 | 0.190 | 367 | 489 | 489 | — |
| 4 | 90:0.50:9.5 | 9.7 | 0.240 | 464 | 677 | 586 | 20 |
| 5 | 75:1.25:23.75 | 10.2 | 0.293 | 566 | 918 | 896 | 83 |
| 6 | 50:2.50:47.5 | 6.7 | 0.467 | 903 | 2329 | 1412 | 189 |
| 7 | 25:3.75:71.25 | 24.0 | 0.423 | 818 | 1836 | 3961 | 710 |
| Film of Hytrel ® 4056 | — | 0 | 0.763 | 1475 | — | — | — |

The results shown in Table I demonstrate a dramatic improvement in the normalized MVTR of the composites of Examples 4–7 over the MVTR of the pressure sensitive adhesive alone. As the last column demonstrates, in the composite where the pressure sensitive adhesive is an acrylate/N-vinyl-2-pyrrolidone copolymer (IOA/NVP) and the hydrocolloid is poly N-vinyl-2-pyrrolidone (PNVP), the MVTR increased rapidly with increased percentage by weight of the PNVP swollen with glycerol into a gel. Between almost 200 and 700 percent improvement was achieved by incorporating between 50 and 75 weight percent of gel in the composite. Less than 6% of the gel was hydrocolloid, demonstrating significant MVTR with a high loading of swelling agent in the gel: a ratio of hydrocolloid to swelling agent of 1:19 (1.25:23.75).

EXAMPLES 8–17

Determination of Relative Skin Adhesion Using Another Composite Formulation

Consequential to the dramatic improvement in MVTR, it was important to know what change in skin adhesion had occurred at these high gel loadings in the composite and the high weight percent ratio of swelling agent to hydrocolloid in the gel. A central composite design was utilized to assess the influence on skin adhesion of the gel weight fraction in the composite over the range of 0–50% and percent hydrocolloid in the gel over the ratios of 1:20 to 1:1. The hydrocolloid of Example 8 was used in the following formulations, examples 9–17.

EXAMPLE 8

Crosslinked PNVP Hydrocolloid

A solution consisting of 0.16 parts of 3,3'-ethylidene bis (N-vinyl-2-pyrrolidone), 1.0 parts 2-hydroxy-2-methyl-1-phenyl-1-propanone, (serving as the photoinitiator) and 100 parts of N-vinyl-2-pyrrolidone was polymerized and processed in the manner described in Example 1.

EXAMPLES 9–17

Example formulations 9–17 were prepared by the following procedure. The cross-linked poly (N-vinyl pyrrolidone) samples of Example 8 in the various weights shown in Table II were first swollen in a solution of glycerol and water in the parts by weight shown in Table II to achieve approximately 5% PNVP polymer solids, providing a weight ratio of 1:20. This produced a thick gel paste which was easily dispersible.

The various gel particles of Examples 9–17 were sheared with a "Laboratory Dispersator" mixer into a mixture of the pressure sensitive adhesive prepared according to Example 2.

An additional 20 parts by weight of n-heptane was then added as the mixture was sheared vigorously for between 5 and 10 minutes using a "Laboratory Dispersator" mixer. Following shearing, the mixture was allowed to stand one minute to eliminate bubbles from the solution and was coated on the H. P. Smith "Poly Slik S-8003" brand release liner. The composite was dried 10 minutes at room temperature and oven dried at 93° C. for one hour to remove the volatile n-heptane and ethyl acetate and the water from the gel and adhesive in the composite.

TABLE II

| Gel and Composite Formulation (Parts by Weight) | | | | |
| --- | --- | --- | --- | --- |
| Example | Glycerol | Deionized Water | PNVP of PSA of | | Composite Coating mg/cm$^2$ |
| | | | Ex. 8 | Ex. 2* | |
| 2 | 0 | 0 | 0 | 100.0 | 5.2 |
| 9 | 1.08 | 15.32 | 0.82 | 98.1 | 4.1 |
| 10 | 1.68 | 2.72 | 0.22 | 98.1 | 3.4 |
| 11 | 3.85 | 73.15 | 3.85 | 92.3 | 2.5 |
| 12 | 5.58 | 36.82 | 2.12 | 92.3 | 3.4 |
| 13 | 5.58 | 36.82 | 2.12 | 92.3 | 3.6 |
| 14 | 7.31 | 0.49 | 0.39 | 92.3 | 4.6 |
| 15 | 8.89 | 127.31 | 6.81 | 84.3 | 4.3 |
| 16 | 13.88 | 22.52 | 1.82 | 84.3 | 6.6 |
| 17 | 14.50 | 95.50 | 5.50 | 80.0 | 4.0 |

*The PSA weight is one quarter of the amount in this column because it is a 25% solution of PSA solids.

Two coated adhesive samples of each of the above examples were removed from the release liner and were hot laminated at 93° C. and 3.5 Kg/cm$^2$ pressure to two different films, 28 microns thick, prepared from "Hytrel 4056" and "Hytrel 3548" brand polyester elastomers commercially available from DuPont.

Skin adhesion of the samples laminated with film prepared from "Hytrel 4056" polyester elastomer was measured initially, after four hours and after 24 hours.

The following protocol was used. The backs of six subjects were first wiped clean with a 70:30 solution of isopropanol:water. Once the alcohol had dried, six samples, per formulation, 1.3 centimeters by 10 centimeters, were applied to each subject's back.

Two tapes of each formulation were removed per removal time using a 180 degree peel at 30.5 centimeters per minute at $T_o$ (within ten minutes of application), $T_4$ (after four hours), and $T_{24}$ (after 24 hours). Then results of both samples for each time interval were averaged and reported as grams per centimeters in Table III.

The second skin panel test evaluated skin adhesion to sweaty skin using samples of Examples 2, 9–17 laminated to "Hytrel 3548" film prepared from polyester elastomer. The skin was not prepped with alcohol.

Two samples, per formulation, 1.3 centimeters by 10 centimeters were applied, to each of six subjects having dry skin. The subjects road a stationary bicycle for ten minutes in order to begin sweating. Two more samples were applied to the subjects' now wet back. The subjects then road the bike for 20 additional minutes, to continue sweating. Following this time, all of the samples were removed in the same manner at 180 degree peel at 30.5 centimeters per minute. The 180° peel force results were averaged and reported in Table III as applied to dry skin and applied to wet skin. An additional and noteworthy observation was that in none of the samples was there edge lift or, with one exception, any residue left on skin.

TABLE III

| | | SKIN ADHESION | | | | |
|---|---|---|---|---|---|---|
| | | 180° Peel Strength | | | 180° Peel Strength | |
| Example | Wieght Fraction Ratio PSA:Hydrocolloid:Swelling Agent | $T_0$ g/cm | $T_4$ Hours g/cm | $T_{24}$ Hours g/cm | Applied Dry g/cm | Applied Wet g/cm |
| 2 | 100:0:0 | 62 | 103 | 114 | 53 | 45 |
| 9 | 92.8:3.1:4.1 | 52 | 87 | 102 | 54 | 43 |
| 10 | 92.8:0.8:6.4 | 52 | 87 | 99 | 46 | 40 |
| 11 | 75:12.5:12.5 | 49 | 83 | 109 | 47 | 42 |
| 12 | 75:6.9:18.1 | 47 | 88 | 98 | 45 | 34 |
| 13 | 75:6.9:18.1 | 50 | 85 | 100 | 43 | 35 |
| 14 | 75:1.25:23.75 | 51 | 91 | 94 | 47 | 37 |
| 15 | 57.3:18.5:24.2 | 42 | 82 | 80 | 40 | 34 |
| 16 | 57.3:5:37.7 | 63 | 96 | 52* | 56 | 41 |
| 17 | 50:13.75:35.25 | 49 | 89 | 84 | 49 | 41 |

*Trace of glycerol residue

It is apparent that the incorporation of 25% weight fraction of gel to the composite (Examples 11–14) had only a slight impact on skin adhesion of the composite. Even levels of 50% weight fraction of gel (Example 17) resulted in little change to the skin adhesiveness of the composite of various weight fractions. Skin adhesiveness did not vary considerably whether applied dry, applied wet, or maintained on the skin for a few minutes, four hours, or one day.

Equally surprising was that residuing and lifting was not a problem, except for Example 16 which left a trace of glycerol residue, and even then only after 24 hours of continuous use.

These results confirmed that this composite truly incorporated the MVTR benefits of gel polymers with almost no degradation in adhesive performance of acrylate adhesives.

EXAMPLES 18–21

Incorporation Of Antimicrobial Agents Into The Composites

The purpose of the following examples 18–21, was to demonstrate the dramatic increase in antimicrobial activity even at relatively low loadings of gel, 25% by weight fraction of gel in the gel-adhesive composite, (i.e., excluding the weight of the antimicrobial agent until the weight fractions of gel-adhesive composite were determined.)

Controls were used for comparing the performance of the antimicrobial containing composite. These controls included "Ioban ™ 2" brand antimicrobial film, the adhesive thereof containing 2% iodine; "Opsite CH ™" brand incise drape, the adhesive thereof containing 5% chlorhexidine acetate; and "Steri-Drape ™ 2" incise drape, the adhesive thereof not containing an antimicrobial agent. "Ioban 2 ™" and "Steri-Drape ™ 2" brand incise drape are both commercially available from 3M Company, St. Paul, Minn. "Opsite CH ™" brand incise drape is commercially available from Smith and Nephew Medical Limited, Hull, HU32BN England.

EXAMPLES 18–21

These examples utilized the cross-linked poly (N-vinyl pyrrolidone) of Example 8 which was first swollen by a solution containing water, glycerol and antimicrobial (e.g. iodine and sodium iodide or chlorhexidine gluconate solution) in the parts by weight shown in Table IV.

The swollen gel paste was then dispersed into the acrylic adhesive solution of Example 2 with a "Laboratory Dispersator" mixer, vigorously for between 5 and 10 minutes until the gel was fully mixed. An additional 20 parts (wt.) of n-heptane is added to assist in the dispersion process. The solution was sheared for several minutes or until uniform and free of agglomerates. The mixture was allowed to stand for one minute, to eliminate bubbles prior to coating on a H. P. Smith "Poly Slik S-8003" brand release liner. The composite was dried 10 minutes at room temperature and then oven dried at 80° C. for one hour. The coated adhesive samples were removed from the release liner and hot laminated at 93° C. at 3.5 Kg/cm$^2$ pressure to 28 microns (1.1 mil) thick film prepared from "Hytrel$^R$ 3548" brand elastomer.

TABLE IV

| Gel and Composite Formulation (Parts by Weight) | | | | | | | |
|---|---|---|---|---|---|---|---|
| Example | Glycerol | Distilled Water | PNVP of Ex. 8 | Iodine | NaI | 20% CHg* in Water | PSA of Ex. 2** |
| 18 | 5.58 | 36.82 | 2.12 | 0.61 | 0.77 | — | 92.30 |
| 19 | 13.88 | 22.52 | 1.82 | 0.78 | 0.93 | — | 84.30 |
| 20 | 5.58 | 30.67 | 2.12 | — | — | 7.65 | 84.90 |
| 21 | 13.88 | 15.07 | 1.82 | — | — | 9.25 | 77.56 |

*20% chlorhexidine gluconate in water.
**25% weight percent of PSA solids in grams of PSA solution Antimicrobial activity In Vitro testing results for the controls and the laminated composites of Examples 8–21 are presented in Table V below. The Ulrich procedure was used for the test, according to the procedure identified in *Infection in Surgery*, August 1984, 569–574, the disclosure of which is incorporated by reference herein, as modified below.

Ulrich Procedure For Determining Antibacterial Activity Of Transparent Dressings Specimens were handled aseptically on a laminar flow clean bench which was disinfected with isopropanol prior to use. The laminated composites were each cut into one inch squares. Liner was removed with the aid of sterile forceps and the film backing placed coating-up on a raised surface in the bottom of a moist chamber.

Just prior to application, Streptococcus faecalis was grown on m-enterococcus agar. The suspension was adjusted turbidimetrically to contain at least $10^8$ bacteria/ml and a viable count was made by the pour-plate method. A micropipette was employed to deposit and distribute 0.05 ml of this suspension on the adhesive surface; the contents were first spotted over the entire surface and then spread evenly with the pipette tip.

At time intervals of 10, 30, 60, and 90 minutes the seeded squares were removed and separately placed in blenders containing 100 ml of 6.25 fold strength "Difco" brand neutralizing buffer commercially available from Baxter Health Care Corp. This concentration is not inhibitory for most bacteria and negates transfer of both antimicrobials to the rinsing fluid. The samples were essentially macerated by five minutes agitation at full speed. An aliquot of rinsing fluid was decanted from the blender cup and exponentially diluted in sterile physiological saline. The following dilutions were plated in m-enterococcus agar to provide viable counts: undiluted, $10^{-1}$, $10^{-2}$, $10^{-3}$, $10^{-4}$, $10^{-5}$; an initial dilution of $10^{-2}$ was imposed on these counts by the rinsing fluid. Plates were incubated overnight at 35° C. and enumerated with the Biotran II automatic colony counter.

The $\log_{10}$ reduction in bacterial numbers was determined by the numerical difference between the inoculum and recovery values. Duplicate platings on duplicate specimens were averaged to obtain final numbers.

microbial film control, but the composite of Examples 18 and 19 showed comparable iodine activity.

EXAMPLES 22-33

The next Examples 22-33 demonstrated the broad flexibility in formulating these gel-adhesive composites. Table VI shows the formulations of the composites in parts by weight having the antimicrobial agent therein.

The procedure for preparing these examples was the same as that outlined in Examples 18-21, except that the percent of PSA solids was slightly higher resulting in recalculation of the weight fraction of the PSA in the final composite.

TABLE VI

Gel and Composite Formulations (Parts by Weight)

| Example | Glycerol | Distilled Water | PNVP of Ex. 8 | 20% CHg* in water | PSA (27.6% solids) of Example 2 |
|---|---|---|---|---|---|
| 22 | 0.85 | 14.55 | 0.77 | 3.7 | 58.38 |
| 23 | 2.15 | 14.65 | 0.84 | 3.9 | 57.02 |
| 24 | 1.41 | 29.99 | 1.57 | 3.9 | 66.95 |
| 25 | 5.69 | 22.71 | 1.42 | 4.6 | 52.88 |
| 26 | 3.74 | 63.89 | 3.38 | 4.6 | 52.88 |
| 27 | 3.74 | 63.89 | 3.38 | 4.6 | 52.88 |
| 28 | 3.74 | 63.86 | 3.38 | 4.6 | 52.88 |
| 29 | 3.74 | 63.86 | 3.38 | 4.6 | 52.88 |
| 30 | 1.78 | 105.02 | 5.34 | 4.6 | 52.88 |
| 31 | 9.40 | 63.93 | 3.67 | 5.6 | 46.93 |
| 32 | 4.32 | 170.71 | 8.75 | 5.6 | 46.93 |
| 33 | 8.59 | 146.81 | 7.77 | 6.1 | 43.64 |

*20% chlorhexidine gluconate in water.

Table VII demonstrated that even as the weight fraction of the gel was varied from 10-60%, acceptable

TABLE V

IN VITRO ANTIMICROBIAL EFFICACY
Log Reduction (S. faecalis)

| Example | Weight Fraction Ratio PSA:Hydrocolloid:Swelling Agent | Antimicrobial | Ulrich Procedure Antimicrobial Activity | | | |
|---|---|---|---|---|---|---|
| | | | 10 min | 30 min | 60 min | 90 min |
| 18 | 75:6.88:18.12 | 2% Iodine | 1 | 5 | —* | 4 |
| 19 | 57.3:5:37.7 | 2% Iodine | Nil | 3 | —* | 6 |
| 20 | 73.4:7.3:19.3 | 5% Chlorhexidine | 3 | 5 | —* | 5 |
| 21 | 55.25:5.2:39.55 | 5% Chlorhexidine | 2 | 2 | —* | 6 |
| "Ioban TM 2" Antimicrobial Film | — | 2% Iodine | Nil | 3 | 5 | 5 |
| "OPSITE TM CH" Drape | — | 5% Chlorhexidine | 0 | —* | 0 | —* |
| "STERI-DRAPE TM 2" Drape | — | (NO ANTIMICROBIAL) | 0 | 0 | —* | 0 |

*Not measured

The results indicate that chlorhexidine did not appear to be active in the "Opsite TM CH" incise drape control but was very active in the composite of Example 20 and 21. Iodine was very active from the "Ioban TM 2" antiadhesion and in most cases superior antimicrobial gel-adhesive composites were possible.

TABLE VII

In Vitro Test vs. strep. faecalis (ATCC 10741)
And Skin Adhesion

| Example | Weight Fraction Ratio PSA:Hydrocolloid:Swelling Agent | 180° Peel Strength | | | Ulrich Procedure Antimicrobial Activity | |
|---|---|---|---|---|---|---|
| | | $T_0$ Hour g/cm | $T_1$ Hour g/cm | $T_6$ Hour g/cm | 6 min | 10 min |
| 22 | 90.9:4.3:4.8 | 45.9 | 81.1 | 97.1 | 1.0 | 5.0 |
| 23 | 84:4.5:11.5 | 46.1 | 78.3 | 82.5 | 2.0 | 5.0 |
| 24 | 86.1:7.3:9.0 | 43.9 | 74.9 | 82.8 | 2.0 | 5.0 |
| 25 | 67.3:6.5:26.2 | 51.6 | 84.9 | 101.0 | 2.0 | 4.0 |
| 26 | 67.2:15.6:17.2 | 45.6 | 66.1 | 79.1 | 2.0 | 5.0 |
| 27 | 67.2:15.6:17.2 | 45.4 | 66.2 | 79.2 | 2.0 | 5.0 |
| 28 | 67.2:15.6:17.2 | 45.4 | 66.8 | 79.8 | 2.0 | 5.0 |
| 29 | 67.2:15.6:17.2 | 45.4 | 66.1 | 78.7 | 2.0 | 5.0 |
| 30 | 67.2:24.6:8.2 | 20.8 | 36.1 | 61.8 | 2.0 | 5.0 |
| 31 | 49.8:14.1:36.1 | 42.8 | 78.0 | 86.6 | 3.0 | 5.0 |

TABLE VII-continued

In Vitro Test vs. *strep. faecalis* (ATCC 10741) And Skin Adhesion

| Example | Weight Fraction Ratio PSA:Hydrocolloid:Swelling Agent | 180° Peel Strength | | | Ulrich Procedure Antimicrobial Activity | |
|---|---|---|---|---|---|---|
| | | $T_0$ Hour g/cm | $T_1$ Hour g/cm | $T_6$ Hour g/cm | 6 min | 10 min |
| 32 | 49.8:33.6:16.6 | 14.6 | 25.8 | 43.9 | 1.0 | 5.0 |
| 33 | 42.4:27.4:30.2 | 31.9 | 56.9 | 73.2 | 2.0 | 3.0 |
| "Ioban TM 2" Antimicrobial Film | 100:0:0 | 54.8 | 71.1 | 88.6 | Nil | <1.0 |

As can be seen by referring to Table VII, there was no significant variance among the various gel-adhesive composites as to the antimicrobial activity. Indeed throughout a broad range of weight fractions of the gel, the antimicrobial activity was consistently excellent and compares favorably with "Ioban TM 2" brand antimicrobial film, which is an iodine antimicrobial incise drape without gel therein.

EXAMPLES 34–44

Necessity Of Hydrocolloid And Non-Volatile Swelling Agent

The following examples illustrate the importance of swelling the hydrocolloid with a non-volatile swelling agent. Example formulations 35, 36, 39, and 40 were prepared by the same procedure as outlined for Examples 9–17, according to the formulations identified in Table VIII, with the exception that the coatings were dried 30 min. at 22° C. followed by oven drying for 20 min. at 80° C. Example formulations 37, 38, 41, and 42 were prepared according to the same procedure as Examples 35, 36, 39, and 40, except that in the formulation of the hydrocolloid, no crosslinking agent was used. Example 34 was a repeat example of pressure sensitive adhesive, and Example 44 was a comparison example mixing the swelling agent without hydrocolloid into the adhesive.

TABLE VIII

| | | Gel and Composite Formulations (Parts by Weight) | | | | |
|---|---|---|---|---|---|---|
| Example | Glycerol | Deionized Water | Crosslinked Hydrocolloid of Example 8 | Linear PNVP (360,000 M.W.) | PSA (28% Solids) of Example 2 | Heptane |
| 34 | 0 | 0 | 0 | 0 | 50.0 | 0 |
| 35 | 7.0 | 30.5 | 3.0 | 0 | 107.1 | 20.3 |
| 36 | 14.0 | 61.0 | 6.0 | 0 | 71.4 | 21.4 |
| 37 | 7.0 | 5.0 | 0 | 3.0 | 107.1 | 29.5 |
| 38 | 14.0 | 10.0 | 0 | 6.0 | 71.4 | 35.5 |
| 39 | 0 | 0 | 5.0 | 0 | 53.6 | 21.1 |
| 40 | 0 | 0 | 5.0 | 0 | 35.7 | 19.3 |
| 41 | 0 | 0 | 0 | 5.0 | 53.6 | 10.8 |
| 42 | 0 | 0 | 0 | 5.0 | 35.7 | 19.3 |
| 43 | 10.0 | 0 | 0 | 0 | 107.1 | 22.2 |
| 44 | 20.0 | 0 | 0 | 0 | 71.4 | 19.7 |

The dried adhesives were hot laminated at 93° C. to 28 micron (1.1 mil) thick film prepared from "Hytrel$^R$ 4056" brand elastomer film. These samples were evaluated for T-Peel adhesion to 20 micron thick low density polyethylene film. Moisture vapor transmission rates were also determined in the same manner as described in Examples 4–7. The results are reported in Table IX below.

T-peel tests were performed on each sample by using a variation of ASTM D 1876 on an Instron Model 1122 stress analyzer. The samples were cut to 2.54 cm by 10.2 cm, removed from the release liner, and laminated with a 2.25 Kg roller onto 20 micron thick low density polyethylene (LDPE) film. Six samples for each test were made and tested, the averaged values were reported. The samples were tested under two sets of conditions. The first set of conditions was to age the samples 10 days at room temperature (22° C.) prior to testing. The second set of conditions was to age the samples at 50% relative humidity and 21° C. for 6 days. The jaw separation speed on the Instron Model 1122 stress analyzer was 25.4 cm/min.

TABLE IX

| Example | Weight Fraction Ratio PSA:Hydrocolloid:Swelling Agent | T-Peel Adhesion (g/cm) | | Laminate MVTR g/m²/24 hours |
|---|---|---|---|---|
| | | LDPE 22° C. | LDPE 21° C./50 R.H. | |
| 34 | 100:0:0 | 68 | 59 | 408 |
| 35 | 75:7.5:17.5 | 68 | 63 | 619 |
| 36 | 50:15:35 | 80 | 114 | 797 |
| 37 | 75:7.5:17.5 | 54 | 52 | 856 |
| 38 | 50:15:35 | 68 | 79 | 1066 |
| 39 | 75:25:0 | 66 | 61 | 800 |
| 40 | 66.7:33.3:0 | 23 | 20 | N/A* |
| 41 | 75:25:0 | 45 | 38 | 988 |
| 42 | 66.7:33.3:0 | 11 | 25 | N/A* |
| 43 | 75:0:25 | 61** | 59** | 533 |
| 44 | 50:0:50 | 66** | 70** | 1001 |
| Film of "Hytrel ®" | — | | — | 1376 |

TABLE IX-continued

| Example | Weight Fraction Ratio PSA:Hydrocolloid:Swelling Agent | T-Peel Adhesion (g/cm) LDPE 22° C. | LDPE 21° C./50 R.H. | Laminate MVTR g/m²/24 hours |
|---|---|---|---|---|
| 4056" brand polyester elastomer | | | | |

*Samples without defects to the adhesive could not be made.
**Surface of sample showed glycerol residual which bloomed to the surface.

Examples 35 and 36 utilized crosslinked PNVP hydrocolloid while Examples 37 and 38 utilized uncrosslinked PNVP hydrocolloid. By comparison, Examples 35 and 38 utilized non-volatile glycerol while Examples 39-42 utilized no swelling agent, with a further comparison of crosslinked hydrocolloids in Examples 39 and 40 and uncrosslinked hydrocolloids in Examples 41 and 42. Finally, Examples 43 and 44 used no hydrocolloid with unacceptable results footnoted.

The use of a swelling agent in the gel (Examples 35-38) allowed the composite to substantially retain or even increase the adhesiveness of the pressure sensitive adhesive. For example, the T-Peel adhesive strength on LDPE at 22° C. of Example 36 is greater than the IOA/NVP PSA of Example 34, the unswollen stoma-type adhesives of Example 39 and 40 using crosslinked PNVP hydrocolloid, and the unswollen stoma-type adhesives of Examples 41 and 42 using uncrosslinked PNVP hydrocolloid. A comparable favorable result was obtained after aging in humid conditions. And MVTR was nearly twice the amount as that of the PSA alone of Example 34. The comparative results for Examples 35, 37 and 38 were not as dramatic. But generally the adhesive strength of these Examples were comparable to the pressure sensitive adhesive of Example 34 and the MVTR is 150-175% percent greater.

Table IX also shows the comparison of crosslinked PNVP vs. uncrosslinked PNVP both swollen into a gel and unswollen as a hydrocolloidal material in a stoma-type adhesive. The T-Peel strength on LDPE results were greater for crosslinked PNVP than the uncrosslinked PNVP, both in dry and for humid conditions. Thus, crosslinked PNVP is preferred to uncrosslinked PNVP. Examination of the MVTR results of crosslinked and uncrosslinked PNVP showed that uncrosslinked PNVP and crosslinked PNVP are acceptable and superior to the adhesive of Example 34.

Table IX also shows the unacceptable results of the attempt to formulate a composite without the presence of hydrocolloid. Examples 43-44 showed the effects of incompatible blooming of the glycerol to the surface of the composition, an unacceptable condition. Further, these adhesion values shown for Examples 43-44 will fall dramatically as the composite ages and more glycerol blooms to the surface.

EXAMPLES 45-53

Composites Prepared From A Latex Of Hydrophobic PSA In An Aqueous Solution

These examples utilized a latex base PSA, such that the hydrocolloid was placed in the continuous water phase. The examples demonstrated the superior MVTR performance of composite prepared by this technique and the importance of the swelling agent to the composite.

The formulations were prepared by first swelling the PNVP in the glycerol and water. The swollen gel was then blended into a PSA latex ("Rhoplex$^R$ E-1960D 53 0% N. V.", available from Rohm & Haas Co. Philadelphia, Pa.) by a "Laboratory Dispersator" mixer from Premier Mill Corporation. The final non-volatiles were calculated and a coating thickness was estimated to produce 80 microns of dried composite. The samples were coated on release liner and dried at 22° C. for 30 min followed by 20 min. at 80° C. The dried composite was hot laminated at 93° C. to 28 micron thick film prepared from "Hytrel$^R$ 4056" brand polyester elastomer. Specific formulations in the latex are identified in Table X, and T-Peel strength and MVTR results, measured in the same manner as for Examples 34-44 are reported in Table XI.

TABLE X

| Example | Gel and Composite Formulations (Parts By Weight) | | | | |
|---|---|---|---|---|---|
| | Glycerol | Deionized Water | PNVP of Example 8 | PNVP (360,000 M.W.) | 53% Solids "Rhoplex ® E-1960D" Latex |
| 45 | 0 | 0 | 0 | 0 | 50.0 |
| 46 | 7.0 | 45.1 | 3.0 | 0 | 56.6 |
| 47 | 14.0 | 58.3 | 6.0 | 0 | 37.7 |
| 48 | 7.0 | 33.4 | 0 | 3.0 | 56.6 |
| 49 | 14.0 | 42.3 | 0 | 6.0 | 37.7 |
| 50 | 0 | 35.1 | 2.5 | 0 | 14.2 |
| 51 | 0 | 48.4 | 5.0 | 0 | 9.4 |
| 52 | 0 | 12.0 | 0 | 5.0 | 28.3 |
| 53 | 0 | 18.0 | 0 | 5.0 | 9.4 |
| Film of "Hytrel ® 4056" brand polyester elastomer | — | — | — | — | — |

TABLE XI

| Example | Weight Fraction Ratio PSA:Hydrocolloid:Swelling Agent | T-Peel Adhesion (g/cm) LDPE 22° C. | LDPE 21° C./50 R.H. | Laminate MVTR g/m²/24 hours |
|---|---|---|---|---|
| 45 | 100:0:0 | 66 | 95 | 619 |
| 46 | 75:7.5:17.5 | 75 | 98 | 948 |
| 47 | 50:15:35 | 127 | 198 | 1442 |
| 48 | 75:7.5:17.5 | 39 | 139 | 928 |
| 49 | 50:15:35 | 80 | 93 | 1350 |
| 50 | 75:25:0 | 13 | 4 | 1178 |
| 51 | 50:50:0 | 0 | 0 | 1211 |
| 52 | 75:25:0 | 0 | 0 | 1205 |
| 53 | 50:50:0 | 0 | 0 | 1198 |
| Film of "Hytrel ® 4056" brand | — | — | — | 1376 |

TABLE XI-continued

| | | T-Peel Adhesion (g/cm) | | |
|---|---|---|---|---|
| Example | Weight Fraction Ratio PSA:Hydrocolloid:Swelling Agent | LDPE 22° C. | LDPE 21° C./50 R.H. | Laminate MVTR g/m²/24 hours |
| polyester Elastomer | | | | |

Examples 46 and 47 demonstrated the use of swollen gel of crosslinked PNVP. Examples 48 and 49 demonstrated the use of swollen gel of uncrosslinked PNVP. Examples 50 and 51 demonstrated the use of gel of crosslinked PNVP temporarily swollen by water. Examples 52 and 53 demonstrated the use of gel of uncrosslinked PNVP temporarily swollen by water.

Again, a comparison of the T-Peel strength on LDPE of the various examples with LDPE aged in dry and wet conditions demonstrated the superior performance of the composites prepared using a non-volatile swelling agent and a crosslinked PNVP hydrocolloid, i.e., Examples 46 and 47. Of the compositions of Examples 50-53 without the non-volatile swelling agent, only the composition of Example 50 has any T-Peel adhesion at all, which amount was vastly inferior to the results for any of the compositions of Examples 46-49.

As shown in Table XI, excellent MVTR was provided by the compositions of Examples 46-49, between

EXAMPLES 54–59

Gel Particle Size Variations On The Composites

The influence of particle size on adhesion and MVTR was studied. The PNVP particles were prepared by grinding the hydrocolloid polymer of Example 8 through a "Retsch Brinkman" grinder at 20,000 rpm and with a ¾ mm grate. The particles were then sized through several wire meshes to provide 3 samples ranging from 25–106 microns, 106–212 microns and 300–600 microns. Due to the very fragile nature of the swollen gels during processing, great care was taken to use minimal shear in blending them into the adhesive latex. With this exception, the Examples of 54–59 were prepared in the same manner as for Examples 45–53. Table XII reports the formulations and Table XIII reports the T-Peel adhesive strength and MVTR of each composite of the Examples, as measured in the same manner as that for Examples 35–44.

TABLE XII

| | Formulations of Gel and Composite (Parts by Weight) | | | | |
|---|---|---|---|---|---|
| Example | Particle Size Range of PNVP of Ex. 8 | Glycerol | Deionized Water | PNVP of Ex. 8 (sized) | 53% Solids "Rhoplex ® E-1960D" Latex |
| 54 | 300–600 microns | 7.0 | 53.0 | 3.0 | 56.6 |
| 55 | 300–600 microns | 14.0 | 76.0 | 6.0 | 37.7 |
| 56 | 106–212 microns | 7.0 | 43.0 | 3.0 | 56.6 |
| 57 | 106–212 microns | 14.0 | 76.0 | 6.0 | 37.7 |
| 58 | 25–106 microns | 7.0 | 43.0 | 3.0 | 56.6 |
| 59 | 25–106 microns | 7.0 | 38.0 | 3.0 | 18.9 |

TABLE XIII

| | Dried | | T-Peel (g/cm) | | |
|---|---|---|---|---|---|
| Example | Hydrocolloid Particle Size | Weight Fraction Ratio of PSA:Hydrocolloid:Swelling Agent | LDPE 22° C. | LDPE 21° C./50 R.H. | Laminate MVTR g/m²/24 hour |
| 54 | 300–600 microns | 75:7.5:17.5 | 148 | 152 | 889 |
| 55 | 300–600 microns | 50:15:35 | 125 | 130 | 1067 |
| 56 | 106–212 microns | 75:7.5:17.5 | 291 | 270 | 790 |
| 57 | 106–212 microns | 50:15:35 | 168 | 148 | 1106 |
| 58 | 25–106 microns | 75:7.5:17.5 | 248 | 273 | 856 |
| 59 | 25–106 microns | 50:15:35 | 164 | 150 | 1310 |
| 45 | No Hydrocolloid | 100:0:0 | 66 | 95 | 619 |
| Film of "Hytrel ®/4056" brand polyester elastomer | | 0 | — | — | 1376 |

1.5 and 2.0 times the MVTR provided by latex-produced PSA of Example 45. While other Examples also had a high MVTR compared with the latex-produced PSA of Example 45, none of them also provided higher T-Peel adhesive strengths than the composite of Example 47.

Data in Table XI also demonstrated by comparison to the data of Table IX that the T-Peel strength of the preferred composites were not adversely affected by the method of preparation of the composite. Whether dispersed into a continuous hydrophobic phase, the results of which are reported in Table IX, or mixed into a hydrophilic latex, the results of which are reported in Table XI, the composites of the present invention provided excellent adhesive strength and high moisture vapor transmission rates.

The results as reported in Table XIII did not demonstrate a definite particle size performance relationship to adhesion. At the 50:15:35 weight fraction ratio (Examples 55, 57, and 59) MVTR increased as the particle size decreased from 300–600 microns to 25–106 microns. However, for composites with less gel dispersed in the adhesive matrix (Examples 54, 56, and 58), even at the same ratio of hydrocolloid to swelling agent, there was no trend between particle size and MVTR.

EXAMPLES 60-64

Other Hydrocolloids In The Gel-Adhesive Composites

The previous examples have all focused on linear or crosslinked poly (N-vinyl pyrrolidone) hydrocolloids swollen with a non-volatile swelling agent. The following examples incorporate two variations in the scope of the invention, a change in the hydrocolloid and a change in the continuous pressure sensitive adhesive matrix.

EXAMPLE 60

Pressure Sensitive Adhesive

This example described a pressure sensitive adhesive blend used as the continuous matrix. The adhesive was composed of 50.0 parts "Krayton$^R$ 1111" brand styrene-isoprene block copolymer from Shell Chem. Co., Houston, Tex. and 70.0 parts "Wingtac$^R$ 95" brand polyterpene resin from Goodyear Tire and Rubber, Akron, Ohio dissolved in 360.0 parts of toluene. The hydrophobic adhesive blend was dissolved in a solvent which phase separated from water.

EXAMPLE 61

Guar Gum Hydrocolloid

To 0.9 parts of guar gum ("Uniguar$^R$ 150" brand guar gum manufactured by Hi-Tek polymers, Clifton, N.J.) was added 2.1 parts glycerol. The guar gum solution was heated for 2 hours at 65° C. to enhance the absorbance of glycerol. The swollen gel was mixed vigorously with a "Laboratory Dispersator" mixer with 36.0 parts of Example 60, until the gel appeared evenly dispersed. The mixture was allowed to stand for one minute for bubbles to escape. The composite was coated on release liner at a thickness of 0.38 mm. The composite was dried 30 min. at 22° C. and 15 min. at 88° C.

The dried composite was then hot laminated at 93° C. to 28 microns thick film prepared from "Hytrel$^R$ 4056" brand elastomer.

EXAMPLE 62

Xanthan Gum Hydrocolloid

To 0.9 parts of Xanthan Gum ("Keltrol$^R$" brand, manufactured by Merck and Co., Inc. San Diego, Calif.) was added 2.1 parts glycerol and the mixture heated for 2 hours at 65° C. to allow the glycerol to swell the xanthan gum. The swollen gel was mixed vigorously as in Example 61 with 36.0 parts of Example 60 until the gel appeared evenly dispersed. The coating, drying and laminating followed the steps of Example 61.

EXAMPLE 63

Hydroxypropyl Methyl Cellulose

To 0.9 parts of Hydroxypropyl Methyl Cellulose (HPMC) ("Methocel$^R$ J75MS" brand HPMC, manufactured by Dow Chemical, Midland, Mich.) was added 2.1 parts glycerol and 0.53 parts deionized water and the mixture was heated at 65° C. for 2 hours to allow the glycerol to swell the HPMC. The mixture was mixed with 36.0 parts of the adhesive of Example 60 vigorously as in Example 61 until the gel appeared evenly dispersed. The coating, drying, and laminating followed the steps of Example 61.

EXAMPLE 64

Alginate

To 2.0 parts sodium Alginate ("Kelgin$^R$ MV" brand, alginate manufactured by Merck & Co, Inc., San Diego, Calif.) were added 2.5 parts CaSO$_4$, 0.8 parts Na$_3$PO$_4$, 20.0 parts glycerol and 60.0 parts deionized water. The sample was mixed and allowed to stand for several hours to form a firm gel. The gel was placed in a "Waring"700 Model #31BL46 brand blender and ground at the uniform speed of the blender to produce small particle sized gels of less than about 200 microns. 67.3 parts of the gel particles were then mixed with 80.0 parts of the adhesive of Example 60 vigorously as in Example 61 until the gel appeared evenly dispersed. The coating, drying and laminating followed the steps of Example 61.

T-Peel and MVTR results for the composites of Examples 60–64 are reported in Table XIV.

TABLE XIV

| Example | Hydrocolloid | Weight Fraction Ratio of PSA:Hydrocolloid: Swelling Agent | T-Peel (g/cm) LDPE 22° C. | T-Peel (g/cm) LDPE 21° C./50 R.H. | Laminate MVTR g/cm$^2$/24 hr | Dried Coating wt. mg/cm$^2$ | MVTR Normalized to 6.64 mg/cm$^2$ Coating wt. |
|---|---|---|---|---|---|---|---|
| 60 | None | 100:0:0 | 200 | 232 | 158 | 3.33 | 84 |
| 61 | Guar Gum | 75:7.5:17.5 | 284 | 307 | 336 | 5.79 | 328 |
| 62 | Xanthan Gum | 75:7.5:17.5 | 166 | 105 | 356 | 7.64 | 393 |
| 63 | HPMC | 75:7.5:17.5 | 182 | 245 | 138 | 7.79 | 159 |
| 64 | Alginate | 53.5:4.3:42.2 | 218 | 279 | 375 | 9.87 | 492 |

Table XIV demonstrated that the T-Peel adhesive strength of a variety of hydrocolloids was in the range of acceptable PSA T-Peel strengths in both dry and wet conditions. But the MVTR of the composites of Examples 61–64 were significantly greater than the PSA of Example 60. Thus, a variety of hydrocolloids were acceptable in the gel-adhesive composite of the present invention.

EXAMPLES 65–71

Other Gel-Adhesive Composites Having Large Weight Fractions Of Gel Therein

The following examples demonstrated the amount of swollen gel which can be dispersed into the pressure sensitive adhesive matrix before the adhesion of the resulting composite suffers. Example formulations 65–70 were prepared by the same procedures outlined in examples 34–44 with the exception that the composites were air dried 15 min at 22° C. and oven dried at 100° C. for 2 hours. Example 71 was mixed and pressed to a thickness of 0.22 mm and laminated to 28 micron thick film prepared from "Hytrel$^R$ 4056" brand polyester elastomer. T-Peel Adhesion to LDPE was measured under the same conditions as that used for Examples 34–44, in dry humidity at 22° C. Table XV identifies the formulations and Table XVI reports the results.

TABLE XV

| Example | Gel and Composite Formulations (Parts by Weight) | | | | | Dried Coating at mg/cm² |
|---|---|---|---|---|---|---|
| | Glycerol | Deionized Water | PNVP of Ex. 1 | PSA (25.0% solids) of Ex. 2 | n-Heptane | |
| 65 | 0 | 0 | 0 | 100.00 | 0 | 5.68 |
| 66 | .75 | 2.50 | .25 | 76.00 | 10.0 | 5.17 |
| 67 | 9.00 | 30.00 | 3.00 | 32.00 | 20.0 | 5.55 |
| 68 | 10.50 | 35.00 | 3.50 | 24.00 | 20.0 | 5.43 |
| 69 | 11.25 | 37.50 | 3.75 | 20.00 | 20.0 | 4.71 |
| 70 | 12.00 | 40.00 | 4.00 | 16.00 | 20.0 | 5.30 |
| 71 | 9.00 | 0 | 3.0 | 0 | 0 | 25 |

TABLE XVI

| Example | Weight Fraction Ratio of PSA:Hydrocolloid: Swelling Agent | T-Peel Adhesion (g/cm) on LDPE |
|---|---|---|
| 65 | 100:0:00 | 66 |
| 66 | 95:1.25:3.75 | 63 |
| 67 | 40:15:45 | 107 |
| 68 | 30:17.5:52.5 | 76 |
| 69 | 25:18.75:56.25 | 68 |
| 70 | 20:20:60 | 49 |
| 71 | 0:75:25 | 8.5 |

As the percentage of PSA decreased, the T-Peel adhesion of the composite against LDPE rose and fell. Except for Example 65 containing no gel, the hydrocolloid:swelling agent weight fraction ratio for the other Examples 66–71 was a constant weight fraction ratio of 1:3. When considering only the results of T-Peel adhesion, the variation of only the weight fractions of the gel to the PSA demonstrated that a possible range of gel weight fractions was from about just greater than 0, about 5, (Example 66) to about 75 percent (Example 69), i.e., the weight fraction sum of the hydrocolloid and the swelling agent. At ratios of PSA/gels ranging from about 40:60 to about 25:75, (Examples 67–69), where the ratio of the hydrocolloid was constant at 1:3, the T-Peel adhesive strength in the gel-adhesive composite even exceeded the T-Peel adhesive strength of the PSA alone.

EXAMPLES 72–78

P Other Gel Weight Fraction Ratio Limits

Example 30 demonstrated a useful formulation containing PNVP hydrocolloid to glycerol swelling agent ratio of 3:1 (24.6:8.2). The skin adhesion results for Example 30 showed less peel adhesion than other compositions such as Examples 25–29 having the same weight fraction of gel in the composite but having a greater weight fraction of swelling agent in the gel.

The following examples demonstrated the acceptable and preferred ranges of the weight fraction ratios of hydrocolloid to swelling agent. T-peel adhesion results measured in the same manner as for Examples 34–44 to low density polyethylene (LDPE) are reported in Table XVIII below.

LDPE is not a perfect skin substitute for adhesion testing but does represent the general trends in adhesion. At a very high hydrocolloid/swelling agent weight fraction ratio, such as 42.5:7.5 or 5.7:1 (Example 78), the adhesive strength was comparable to unswollen hydrocolloids, i.e., see Example 40. Example formulations 72–78 were prepared by the same procedure outlined in examples 65–70 and are identified in Table XVII. T-Peel adhesive strength was measured in the same manner as for Examples 65–71.

TABLE XVII

| Example | Gel and Composite Formulations (Parts by Weight) | | | | | Coating wt mg/cm² |
|---|---|---|---|---|---|---|
| | Glycerol | Deionized Water | PNVP of Ex. 8 | PSA (25.0% solids) Ex. 2 | Heptane | |
| 72 | 7.13 | 3.80 | .38 | 30.0 | 10.0 | 5.36 |
| 73 | 6.75 | 7.50 | .75 | 30.0 | 10.0 | 4.65 |
| 74 | 6.00 | 15.00 | 1.50 | 30.0 | 10.0 | 4.97 |
| 75 | 4.50 | 30.00 | 3.00 | 30.0 | 10.0 | 5.55 |
| 76 | 2.00 | 30.00 | 3.00 | 20.0 | 10.0 | 5.62 |
| 77 | 1.25 | 37.50 | 3.75 | 20.0 | 10.0 | 6.07 |
| 78 | 0.75 | 42.50 | 4.25 | 20.0 | 10.0 | 6.26 |

TABLE XVIII

| Example | Weight Fraction Ratio of PSA:Hydrocolloid: Swelling Agent | T-Peel Adhesion (g/cm) on LDPE |
|---|---|---|
| 70 | 100:0:0 | 66 |
| 72 | 50:2.5:47.5 | 99 |
| 73 | 50:5:45 | 80 |
| 74 | 50:10:40 | 108 |
| 75 | 50:20:30 | 68 |
| 76 | 50:30:20 | 28 |
| 77 | 50:37.5:12.5 | 29 |
| 78 | 50:42.5:7.5 | 25 |
| 40 | 66.7:33.3:0 | 23 |

As illustrated in Table XVIII, the T-Peel strength also rose and fell throughout increasing weight fraction ratios of hydrocolloids to swelling agents. Based on the variation of such weight fraction ratios and a constant weight fraction of the swollen gel in the composite, a desirable range extended from about 1.5:1 to about 1:19 (Examples 72–76) with a preferable range for the better balance of properties being from about 1:1.5 to about 1:19 (Examples 72–75).

EXAMPLES 79–86

Determination Of Acceptable Shear Modulus Of The Gel

The following examples 79–86 quantified the shear modulus range for the gels in the gel-adhesive composites of the present invention. The samples were prepared by mixing powdered poly (N-vinyl pyrrolidone) of example 8 with varying amounts of glycerol. The samples were allowed 24 hours to completely absorb the glycerol, followed by hydraulically pressing the samples between release liners to a thickness of 1 mm. The resultant gel films were cut to 50 mm diameter circles and tested between 50 mm diameter parallel plates at 22° C. on a "Rheometrics Mechanical Spectrometer", Model 605 manufactured by Rheometrics Inc. 1 Possumtown Road, Piscataway, N.J. These details and ASTM D 4065-82 describe the technique used. The Shear Modulus for each samples is reported Table XIX below in dynes/cm² at 1 and 5.6 Rad/sec.

TABLE XIX

Gel and Composite Formulations (Parts by Weight) and Shear Modulus Results

| Example | Weight % Example 8 PNVP | Weight % Glycerol | Shear Modulus (Dynes/cm$^2$ *10$^{-3}$) 1 Rad/Sec. | 5.6 Rad/Sec. |
|---|---|---|---|---|
| 79 | 5 | 95 | 2.95 | 5.13 |
| 80 | 10 | 90 | 7.20 | 10.32 |
| 81 | 20 | 80 | 16.94 | 26.24 |
| 82 | 30 | 70 | 25.22 | 42.24 |
| 83 | 40 | 60 | 41.17 | 74.19 |
| 84 | 50 | 50 | 153.5 | 179.7 |
| 85 | 60 | 40 | 999.4 | 2,068 |
| 86 | 75 | 25 | 6,171 | 6,423 |

Examples 30 and 77 having PNVP as the hydrocolloid showed useful formulations containing PNVP hydrocolloid/swelling agent ratios up to 3:1. Since the shear modulus of the gel will vary with the type of hydrocolloid (e.g. PNVP, alginates, cellulosics) and the choice of non-volatile swelling agent, examples 79–86 were important in defining a desired upper modulus. An upper modulus is desired to assure that the gel particles are soft and pliable in the composites.

There does not appear to be a lower modulus limit; rather there must be at least a minimal amount of hydrocolloid present to prevent the swelling agent from migrating or blooming to the surface of the composite and thereby degrading the adhesive properties thereof. An example of this incompatible blooming was shown by examples 44–45 where no hydrocolloid was present.

The desired upper shear modulus limit for the swollen hydrocolloid was represented by example 86, at $6.2 \times 10^6$ dynes/cm$^2$. The preferred upper shear modulus limit was represented by example 84 at $1.5 \times 10^5$ and the most preferred upper shear modulus limit was represented by example 83 at $41.2 \times 10^3$ dynes/cm$^2$.

EXAMPLES 87 AND 88

Other Swelling Agents

Examples 87 and 88 demonstrated the use of other non-volatile swelling agents in place of glycerol.

EXAMPLE 87

To 3.0 parts of crosslinked poly (N-vinyl pyrrolidone) of example 8 was added 7.0 parts propylene glycol and 30.5 parts of distilled water. Once the solution was absorbed by the PNVP, the gel was mixed vigorously with 35.7 parts of the PSA of example 2 (28.0% solids) and 10.7 parts n-heptane until the hydrocolloid appeared evenly dispersed. The coating, drying and laminating follow the procedure for example 65. The resulting gel-adhesive composite was transparent, very adhesive and had a smooth texture. T-peel adhesion to LDPE was 65 gm/cm, which compares favorably with the use of glycerol, as seen in Examples 6–69 and 72–75.

EXAMPLE 88

To 3.0 parts of crosslinked poly (N-vinyl pyrrolidone) of Example 8 was added 1.0 parts glycerol, 8.6 parts of a 70% sorbitol solution in water and 30.5 parts distilled water. Once the solution was absorbed by the PNVP the gel was mixed vigorously with 35.7 parts of the PSA of Example 2 (28.0% solids) and 10.7 parts n-heptane until the hydrocolloid appeared evenly dispersed. The coating, drying and laminating followed the steps of Example 65. The resulting gel-adhesive composite was transparent, very adhesive and had a smooth texture. T-peel adhesion to LDPE was 66 gm/cm, which compares favorably with the use of glycerol, as seen in Examples 66–69 and 72–75.

In accordance with the Patent Statutes, embodiments of the invention have been described. A series of examples have been provided to illustrate the variety of acceptable components according to the scope of the invention. The invention is not to be limited by the description of the embodiments or examples. There are many variations within the scope of the invention. Consequently, for an understanding of the scope of the invention, reference is made to the following claims.

What is claimed is:

1. A method for preparing a composite of a gel dispersed in a pressure sensitive adhesive matrix having a high moisture vapor transmission rate, comprising:
   (a) grinding hydrocolloid into finely divided particles
   (b) swelling said hydrocolloid particles non-reacting conditions with a non-volatile, hydrophilic swelling agent to fully form swollen discrete hydrocolloid gel particles; and
   (c) dispersing said fully formed gel particles into a hydrophobic solution comprising a pressure sensitive adhesive.

2. A method according to claim 1, further comprising after said dispersing the steps of coating said solution on a release liner and of drying said solution to form a continuous pressure sensitive adhesive matrix having said gel particles dispersed therethrough to form a gel-adhesive composite.

3. A method according to claim 2, further comprising after said coating the step of attaching said composite to a backing material.

4. A method according to claim 2, wherein said swelling further comprises mixing a volatile hydrophilic solvent with said finely divided particles and wherein said drying step removes said volatile hydrophilic solvent from said swollen gel particles, wherein the gel particles have a shear modulus of less than about $6.2 \times 10_6$ dynes/cm$^2$.

5. A method for preparing a composite of gel dispersed in a pressure sensitive adhesive matrix having a high moisture vapor transmission rate, comprising:
   (a) grinding hydrocolloid into finely divided particles;
   (b) swelling said hydrocolloid particles under non-reacting conditions with a non-volatile, hydrophilic swelling agent to fully form swollen discrete hydrocolloid gel particles; and
   (c) dispersing said fully formed gel particles into a latex mixture comprising a pressure sensitive adhesive.

6. A method according to claim 5, further comprising after said dispersing the steps of coating said latex mixture on a release liner and of drying said mixture to form a continuous pressure sensitive adhesive matrix having said gel particles dispersed therethrough to form a gel-adhesive composite.

7. A method according to claim 6, further comprising after said coating the step of attaching said composite to a backing material.

8. A method according to claim 6, wherein said mixing further comprises mixing a volatile hydrophilic solvent with said finely divided particles and wherein said drying step removes said volatile hydrophilic solvent from said swollen gel particles.

* * * * *